(12) United States Patent
Berger et al.

(10) Patent No.: US 8,377,931 B2
(45) Date of Patent: *Feb. 19, 2013

(54) BENZOXAZINE DERIVATIVES AND USES THEREOF

(75) Inventors: Jacob Berger, Los Altos Hills, CA (US); Robin Douglas Clark, Lawai, HI (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 404 days.

This patent is subject to a terminal disclaimer.

(21) Appl. No.: 12/584,373

(22) Filed: Sep. 4, 2009

(65) Prior Publication Data

US 2009/0325950 A1    Dec. 31, 2009

Related U.S. Application Data

(63) Continuation of application No. 11/047,284, filed on Jan. 31, 2005, now abandoned, which is a continuation of application No. 10/435,732, filed on May 9, 2003, now Pat. No. 6,867,204.

(60) Provisional application No. 60/378,003, filed on May 13, 2002.

(51) Int. Cl.
*A61K 31/535*    (2006.01)
*C07D 265/38*    (2006.01)

(52) U.S. Cl. .................................. 514/230.5; 544/105

(58) Field of Classification Search ............. 514/211.09
See application file for complete search history.

(56) References Cited

U.S. PATENT DOCUMENTS

| 6,380,199 | B1 | 4/2002 | Reavill et al. |
| 6,867,204 | B2 * | 3/2005 | Berger et al. ............ 514/211.09 |

FOREIGN PATENT DOCUMENTS

| WO | WO 96/31508 A1 | 10/1996 |
| WO | WO 98/50358 A1 | 11/1998 |
| WO | 9902502 A2 | 1/1999 |
| WO | 9937623 A2 | 7/1999 |
| WO | WO 00/66564 A1 | 11/2000 |
| WO | WO 01/16108 A2 | 3/2001 |
| WO | WO 01/57003 A1 | 8/2001 |

* cited by examiner

*Primary Examiner* — Sreeni Padmanabhan
*Assistant Examiner* — Timothy E Betton
(74) *Attorney, Agent, or Firm* — Robert C. Hall

(57) ABSTRACT

The present invention provides a compound of the formula:

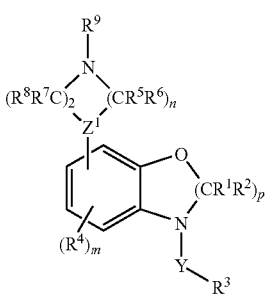

a pharmaceutically acceptable salt or a prodrug thereof, where $R^1$, $R^2$, $R^3$, $R^4$, $R^5$, $R^6$, $R^7$, $R^8$, $R^9$, Y, $Z^1$, m, n, and p are as defined herein. The present invention also provides compositions comprising, methods for using, and methods for preparing Compound of Formula I.

16 Claims, No Drawings

BENZOXAZINE DERIVATIVES AND USES THEREOF

CROSS REFERENCE TO RELATED APPLICATIONS

This application is a continuation of U.S. patent application Ser. No. 11/047,284 filed on Jan. 31, 2005 now abandoned, which is a continuation of U.S. patent application Ser. No. 10/435,732 filed on May 9, 2003 now U.S. Pat. No. 6,867,204, and claims the benefit under Title 35 U.S.C. §119 (e) of U.S. Provisional Application No. 60/378,003, filed on May 13, 2002, the disclosures of which are incorporated herein by reference in their entirety.

FIELD OF THE INVENTION

This invention relates to benzoxazine derivatives, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.,* 1994, 268, pages 1403-14120, D. R. Sibley et al., *Mol. Pharmacol.,* 1993, 43, 320-327, A. J. Sleight et al., *Neurotransmission,* 1995, 11, 1-5, and A. J. Sleight et al., *Serotonin ID Research Alert,* 1997, 2(3), 115-8.

While some 5-HT6 modulators have been disclosed, there continues to be a need for compounds that are useful for modulating 5-HT6.

SUMMARY OF THE INVENTION

The present invention provides compounds of the formula:

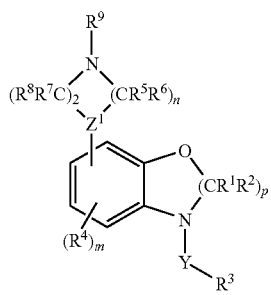

I a pharmaceutically acceptable salt or a prodrug thereof, where
m is an integer from 0 to 3;
each of n and p is independently 2 or 3;
Y is —$SO_2$— or —$SO_2$—N($R^{10}$)—, where $R^{10}$ is hydrogen or lower alkyl;
$Z^1$ is CH or N;
each of $R^1$ and $R^2$ is independently hydrogen or alkyl, or $R^1$ and $R^2$ together with the carbon to which they are attached may form a carbocyclic group with 3 to 6 ring atoms;
$R^3$ is alkyl, aryl, haloalkyl, heterocyclyl, or heteroaryl;
each $R^4$ is independently halo, alkyl, haloalkyl, alkoxy, cyano, —$SO_2R^a$, —C(=O)—$NR^bR^c$, —$SO_2$—$NR^bR^c$, —$SR^b$, —N($R^b$)—C(=O)—$R^c$, —C(=O)—$R^b$, or —N($R^b$)—$SO_2$—$R^a$,
where
each $R^a$ is independently alkyl or haloalkyl, and
each of $R^b$ and $R^c$ is independently hydrogen, alkyl, or haloalkyl,
each of $R^5$, $R^6$, $R^7$, and $R^8$ is independently hydrogen or alkyl; and
$R^9$ is hydrogen, alkyl cycloalkyl, cycloalkylalkyl or benzyl; or $R^9$ and one of $R^5$, $R^6$, $R^7$, or $R^8$ together with the atoms to which they are attached form a heterocycloamino ring with 5 to 7 ring atoms.

The present invention also provides methods for preparing, compositions comprising, and methods for using Compounds of Formula I.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms. Examples of alkyl groups include, but are not limited to, methyl, ethyl, propyl, isopropyl, n-butyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —$OR^z$, wherein $R^z$ is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono- or bicyclic aromatic ring. The aryl group can optionally be substituted with one, two or three, preferably one or two, substituents, wherein each substituent is independently hydroxy, cyano, alkyl, alkoxy, thiol, thioalkyl, halo, haloalkyl, nitro, amino, monoalkylamino, dialkylamino, piperazinyl or piperidinyl, unless otherwise specifically indicated. Examples of aryl moieties include, but are not limited to, optionally substituted phenyl and optionally substituted naphthyl, and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like.

"Cycloalkylalkyl" means a moiety of the formula —R'—R", where R' is alkylene and R" is cycloalkyl as defined herein.

"Disease state" means any disease, condition, symptom, or indication.

The terms "halo" and "halogen" are used interchangeably herein and refer to a substituent fluoro, chloro, bromo, or iodo, preferably fluoro or chloro.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. Heteroaryl can optionally be substituted with one, two, or three, preferably, one or two, substituents, wherein each substituent is independently hydroxy, cyano, alkyl, alkoxy, thioalkyl, halo, haloalkyl, hydroxyalkyl, alkoxycarbonyl, amino, alkylamino, dialkylamino, aminocarbonyl, piperazinyl, piperidinyl or carbonylamino, unless otherwise specifically indicated. Examples of heteroaryl moieties include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, isoindolyl, and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three heteroatoms (chosen from nitrogen, oxygen or sulfur). Heterocyclyl can optionally be substituted with one, two, or three, preferably one or two, substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Examples of heterocyclic moieties include, but are not limited to, morpholinyl, piperazinyl, piperidinyl, pyrrolidinyl, tetrahydropyranyl, and the like.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoro-acetyl, acetamido, benzyl (Bn), benzyloxycarbonyl (car-bobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® v. 2.2. Any open valency on a carbon, nitrogen or oxygen atom on the chemical structures herein should be understood as indicating the presence of a hydrogen.

Compounds of the Invention

In one aspect, the present invention provides a compound of the formula:

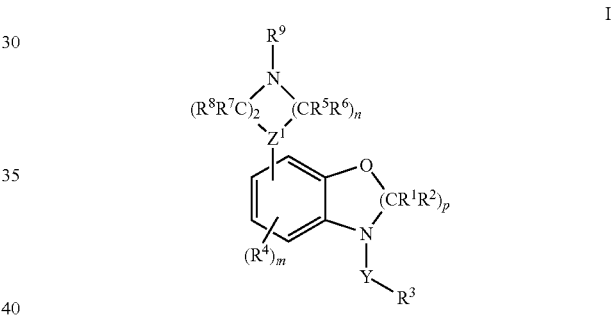

a pharmaceutically acceptable salt or a prodrug thereof, wherein
m is an integer from 0 to 3; preferably, m is 0 or 1;
n is 2 or 3; preferably n is 2;
p is 2 or 3; preferably p is 2;
Y is —S($O_2$)— or —S($O_2$)—N($R^{10}$)—, where $R^{10}$ is hydrogen or lower alkyl; preferably, Y is —$SO_2$—;
$Z^1$ is CH or N; preferably $Z^1$ is N;
each of $R^1$ and $R^2$ is independently hydrogen or alkyl or $R^1$ and $R^2$ together with the carbon to which they are attached may form a carbocyclic group with 3 to 6 ring atoms; preferably, $R^1$ and $R^2$ are hydrogen;
$R^3$ is alkyl, aryl, haloalkyl, heterocyclyl, or heteroaryl; preferably, $R^3$ is aryl or heteroaryl;
each $R^4$ is independently halo, alkyl, haloalkyl, alkoxy, cyano, —$SO_2R^a$, —C(=O)—$NR^bR^c$, —$SO_2$—$NR^bR^c$, —$SR^b$, —N($R^b$)—C(=O)—$R^c$, —C(=O)—$R^b$, or —N($R^b$)—$SO_2$—$R^a$,
where
each $R^a$ is independently alkyl or haloalkyl, and
each of $R^b$ and $R^c$ is independently hydrogen, alkyl, or haloalkyl;
preferably each $R^4$ is independently alkyl or halide; more preferably each $R^4$ is independently chloro or methyl;
each of $R^5$, $R^6$, $R^7$, and $R^8$ is independently hydrogen or alkyl or; preferably $R^5$, $R^6$, $R^7$, and $R^8$ are hydrogen; and R⁹ is hydrogen, alkyl, cycloalkyl, cycloalkylalkyl or benzyl; or R⁹ and one of R⁵, R⁶, R⁷, or R⁸ together with the atoms to which they are attached form a heterocycloamino ring with 5 to 7 ring atoms; preferably, R⁹ is hydrogen or alkyl; more preferably, R⁹ is hydrogen.

It is to be understood that the scope of this invention encompasses not only the various isomers which may exist but also the various mixture of isomers which may be formed. Furthermore, the scope of the present invention also encompasses solvates and salts of Compounds of Formula I.

In one embodiment, Compounds of Formula I are of the formula:

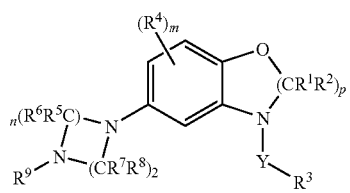

where R¹, R², R³, R⁴, R⁵, R⁶, R⁷, R⁸, R⁹, m, n, p, and Y are those defined herein.

In yet one embodiment, Compounds of Formula I are of the formula:

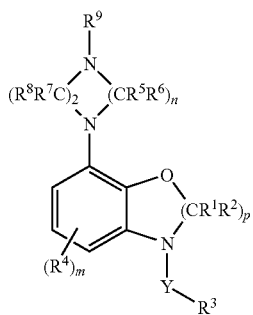

where R¹, R², R³, R⁴, R⁵, R⁶, R⁷, R⁸, R⁹, m, n, p, and Y are those defined herein. More specifically, where n is 2, p is 2, Y is —S(O₂)— and R¹, R², R⁵, R⁶, R⁷ and R⁸ are hydrogen, compounds of Formula I may be represented by the formula:

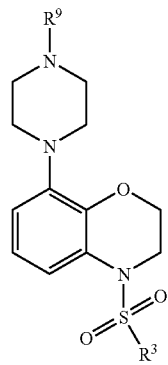

where R³ and R⁹ are as defined herein.

In one particular embodiment, R³ is aryl. Preferably, R³ is optionally substituted phenyl or optionally substituted naphthyl. More preferably, R³ is phenyl, 2-fluorophenyl, 2-chlorophenyl, 3,4-dichlorophenyl, 4-chlorophenyl, 3-chlorophenyl, 4-methoxyphenyl, 3,5-dichlorophenyl, 2,6-dichlorophenyl, 2,4-dichlorophenyl, 3-methanesulfonylaminophenyl, 2-methanesulfonylphenyl, 2-carbamoylphenyl, 3-methanesulfonylphenyl, 4-methanesulfonylphenyl, 3-fluorophenyl, naphthyl, 2,4-difluorophenyl, 2-cyanophenyl, 2-chloro-4-fluorophenyl, 2-methyl-5-fluorophenyl, or 5-chloronaphthyl.

In another specific embodiment, R³ is preferably phenyl or halo-substituted phenyl. More preferably, R³ is phenyl, 2-chloro-substituted phenyl or 2-fluoro-substituted phenyl.

Yet in another embodiment, R³ is heteroaryl. Preferably, R³ is optionally substituted isoquinolinyl, optionally substituted quinolinyl, optionally substituted thiophenyl, optionally substituted benzothiadiazolyl, optionally substituted imidazolyl, or optionally substituted benzoxadiazolyl. More preferably, R³ is quinolin-8-yl, 2-thiophenyl, 5-chlorothiophen-2-yl, isoquinolin-5-yl, benzo[1,2,5]thiadiazol-4-yl, 1-methyl-1H-imidazol-4-yl, or benzo[1,2,5]oxadiazol-4-yl.

Still further, combinations of the preferred groups described herein will form other preferred embodiments. For example, in one particularly preferred embodiment Z¹ is N, m is 1, n is 2, p is 2, R³ is 2-chlorophenyl, Y is —SO₂—, R⁴ is chloro, and R⁵, R⁶, R⁷, and R⁸ are hydrogen. In this manner, a variety of preferred compounds are embodied within the present invention.

Some of the representative Compounds of Formula I are shown in Table 1 below:

TABLE 1

| No. | Name (Autonom ®) | Structure |
|---|---|---|
| 1 | 4-Benzenesulfonyl-6-methyl-8-piperazin-1-yl-3,4-dihydro-2H-benzo[1,4]oxazine | 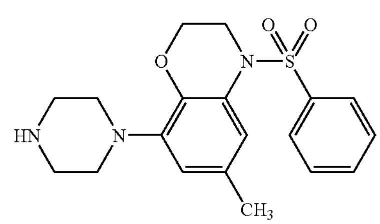 [SMILES: Cc1cc(N2CCNCC2)c2c(c1)N(S(=O)(=O)c1ccccc1)CCO2] |

TABLE 1-continued

| No. | Name (Autonom ®) | Structure |
|---|---|---|
| 2 | 4-(2-Chloro-benzenesulfonyl)-6-methyl-8-piperazin-1-yl-3,4-dihydro-2H-benzo[1,4]oxazine | 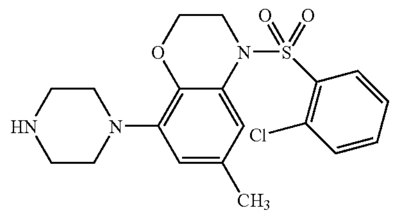 [SMILES: Cc1cc(N2CCNCC2)c2c(c1)N(S(=O)(=O)c1ccccc1Cl)CCO2] |
| 3 | 4-(3,4-Dichloro-benzenesulfonyl)-6-methyl-8-piperazin-1-yl-3,4-dihydro-2H-benzo[1,4]oxazine | 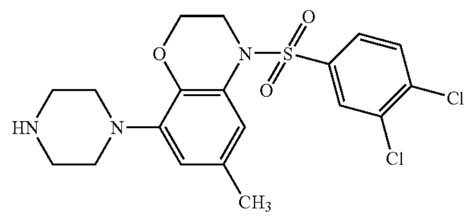 [SMILES: Cc1cc(N2CCNCC2)c2c(c1)N(S(=O)(=O)c1ccc(Cl)c(Cl)c1)CCO2] |
| 4 | 4-(4-Chloro-benzenesulfonyl)-6-methyl-8-piperazin-1-yl-3,4-dihydro-2H-benzo[1,4]oxazine | 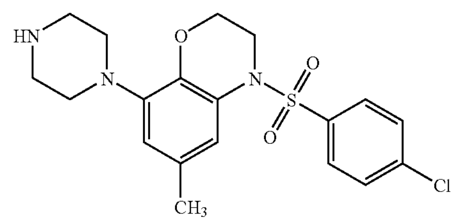 [SMILES: Cc1cc(N2CCNCC2)c2c(c1)N(S(=O)(=O)c1ccc(Cl)cc1)CCO2] |
| 5 | 4-(4-Chloro-benzenesulfonyl)-8-(3,5-dimethyl-piperazin-1-yl)-6-methyl-3,4-dihydro-2H-benzo[1,4]oxazine | 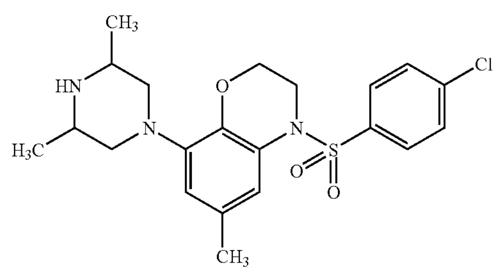 [SMILES: Cc1cc(N2CC(C)NC(C)C2)c2c(c1)N(S(=O)(=O)c1ccc(Cl)cc1)CCO2] |
| 6 | 6-Chloro-4-(2-chloro-benzenesulfonyl)-8-piperazin-1-yl-3,4-dihydro-2H-benzo[1,4]oxazine | 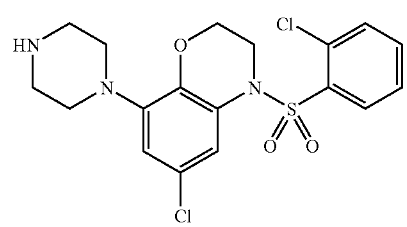 [SMILES: O=S(=O)(c1ccccc1Cl)N1CCOc2c(N3CCNCC3)cc(Cl)cc21] |
| 7 | 4-(3-Chloro-benzenesulfonyl)-6-piperazin-1-yl-3,4-dihydro-2H-benzo[1,4]oxazine | 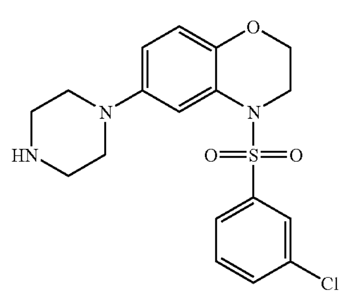 [SMILES: O=S(=O)(c1cccc(Cl)c1)N1CCOc2ccc(N3CCNCC3)cc21] |

TABLE 1-continued

| No. | Name (Autonom ®) | Structure |
|---|---|---|
| 8 | 4-(2-Chloro-benzenesulfonyl)-6-piperazin-1-yl-3,4-dihydro-2H-benzo[1,4]oxazine | 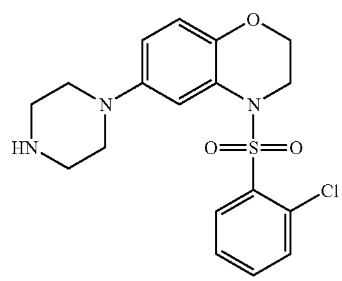 [SMILES: O=S(=O)(c1ccccc1Cl)N1CCOc2ccc(N3CCNCC3)cc21] |
| 9 | 4-(2-Chloro-benzenesulfonyl)-8-piperazin-1-yl-3,4-dihydro-2H-benzo[1,4]oxazine | 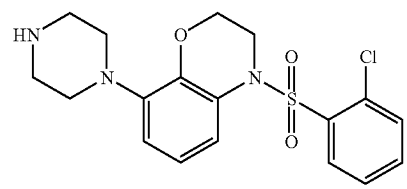 [SMILES: O=S(=O)(c1ccccc1Cl)N1CCOc2c(N3CCNCC3)cccc21] |
| 10 | 4-(4-Chloro-benzenesulfonyl)-8-piperazin-1-yl-3,4-dihydro-2H-benzo[1,4]oxazine | 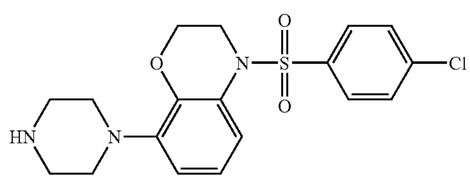 [SMILES: O=S(=O)(c1ccc(Cl)cc1)N1CCOc2c(N3CCNCC3)cccc21] |
| 11 | 4-(4-Methoxy-benzenesulfonyl)-8-piperazin-1-yl-3,4-dihydro-2H-benzo[1,4]oxazine | 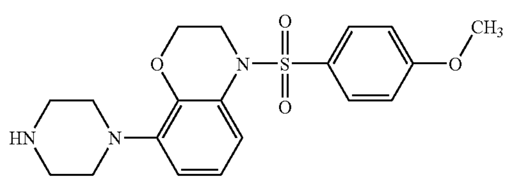 [SMILES: COc1ccc(S(=O)(=O)N2CCOc3c(N4CCNCC4)cccc32)cc1] |
| 12 | 8-Piperazin-1-yl-4-(quinoline-8-sulfonyl)-3,4-dihydro-2H-benzo[1,4]oxazine | 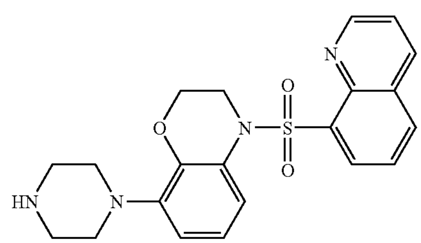 [SMILES: O=S(=O)(c1cccc2cccnc12)N1CCOc2c(N3CCNCC3)cccc21] |
| 13 | 4-(3,4-Dichloro-benzenesulfonyl)-8-piperazin-1-yl-3,4-dihydro-2H-benzo[1,4]oxazine | 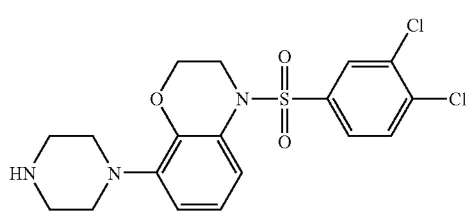 [SMILES: O=S(=O)(c1ccc(Cl)c(Cl)c1)N1CCOc2c(N3CCNCC3)cccc21] |
| 14 | 4-(3-Chloro-benzenesulfonyl)-8-piperazin-1-yl-3,4-dihydro-2H-benzo[1,4]oxazine | 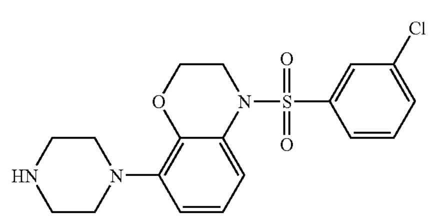 [SMILES: O=S(=O)(c1cccc(Cl)c1)N1CCOc2c(N3CCNCC3)cccc21] |

TABLE 1-continued

| No. | Name (Autonom ®) | Structure |
|-----|------------------|-----------|
| 15 | 4-(3,5-Dichloro-benzenesulfonyl)-8-piperazin-1-yl-3,4-dihydro-2H-benzo[1,4]oxazine | 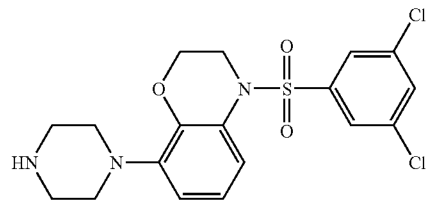 [SMILES: O=S(=O)(c1cc(Cl)cc(Cl)c1)N1CCOc2c(N3CCNCC3)cccc21] |
| 16 | 4-(2,3-Dichloro-benzenesulfonyl)-8-piperazin-1-yl-3,4-dihydro-2H-benzo[1,4]oxazine | 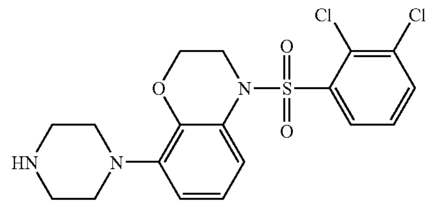 [SMILES: O=S(=O)(c1cccc(Cl)c1Cl)N1CCOc2c(N3CCNCC3)cccc21] |
| 17 | 4-(2,6-Dichloro-benzenesulfonyl)-8-piperazin-1-yl-3,4-dihydro-2H-benzo[1,4]oxazine | 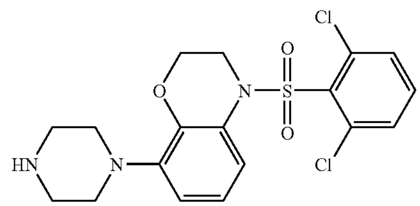 [SMILES: O=S(=O)(c1c(Cl)cccc1Cl)N1CCOc2c(N3CCNCC3)cccc21] |
| 18 | 4-(2,4-Dichloro-benzenesulfonyl)-8-piperazin-1-yl-3,4-dihydro-2H-benzo[1,4]oxazine | 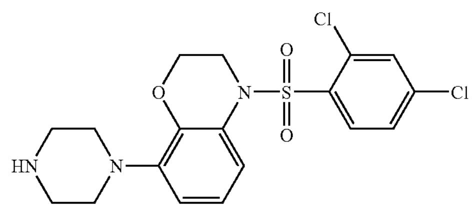 [SMILES: O=S(=O)(c1ccc(Cl)cc1Cl)N1CCOc2c(N3CCNCC3)cccc21] |
| 19 | 4-(4-Chloro-benzenesulfonyl)-6-piperazin-1-yl-3,4-dihydro-2H-benzo[1,4]oxazine | 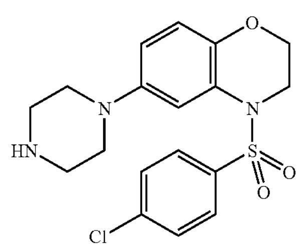 [SMILES: O=S(=O)(c1ccc(Cl)cc1)N1CCOc2ccc(N3CCNCC3)cc21] |
| 20 | N-[3-(8-Piperazin-1-yl-2,3-dihydro-benzo[1,4]oxazine-4-sulfonyl)-phenyl]-methanesulfonamide | 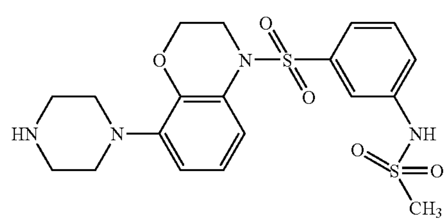 [SMILES: CS(=O)(=O)Nc1cccc(S(=O)(=O)N2CCOc3c(N4CCNCC4)cccc32)c1] |
| 21 | N-[2-(8-Piperazin-1-yl-2,3-dihydro-benzo[1,4]oxazine-4-sulfonyl)-phenyl]-methanesulfonamide | 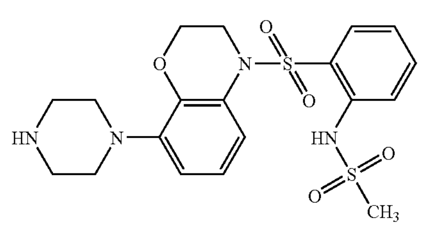 [SMILES: CS(=O)(=O)Nc1ccccc1S(=O)(=O)N1CCOc2c(N3CCNCC3)cccc21] |

TABLE 1-continued

| No. | Name (Autonom ®) | Structure |
|---|---|---|
| 22 | 2-(8-Piperazin-1-yl-2,3-dihydro-benzo[1,4]oxazine-4-sulfonyl)-benzamide | 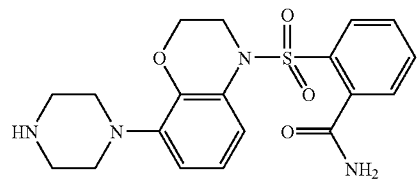 [SMILES: NC(=O)c1ccccc1S(=O)(=O)N1CCOc2c(N3CCNCC3)cccc21] |
| 23 | 4-(3-Methanesulfonyl-benzenesulfonyl)-8-piperazin-1-yl-3,4-dihydro-2H-benzo[1,4]oxazine | 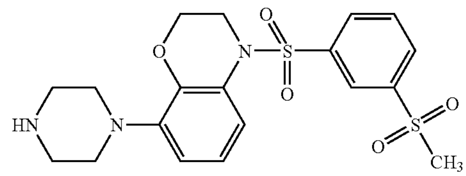 [SMILES: CS(=O)(=O)c1cccc(S(=O)(=O)N2CCOc3c(N4CCNCC4)cccc32)c1] |
| 24 | 6-Chloro-4-(4-methanesulfonyl-benzenesulfonyl)-8-piperazin-1-yl-3,4-dihydro-2H-benzo[1,4]oxazine | 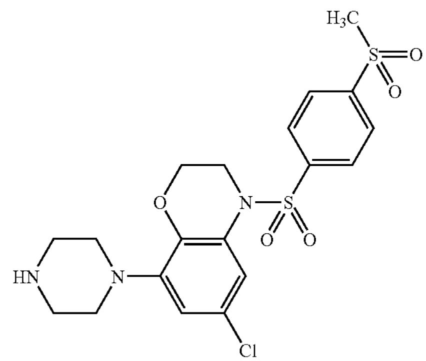 [SMILES: CS(=O)(=O)c1ccc(S(=O)(=O)N2CCOc3c(N4CCNCC4)cc(Cl)cc32)cc1] |
| 25 | 4-Benzenesulfonyl-8-piperazin-1-yl-3,4-dihydro-2H-benzo[1,4]oxazine | 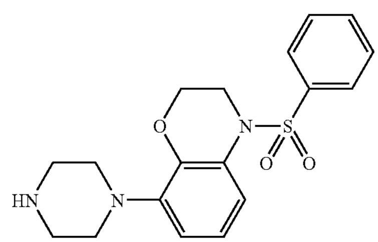 [SMILES: O=S(=O)(c1ccccc1)N1CCOc2c(N3CCNCC3)cccc21] |
| 26 | 4-(2-Fluoro-benzenesulfonyl)-8-piperazin-1-yl-3,4-dihydro-2H-benzo[1,4]oxazine | 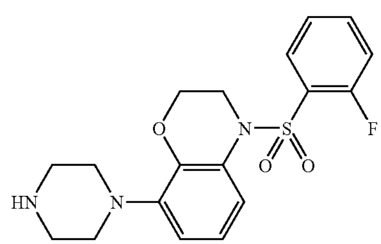 [SMILES: O=S(=O)(c1ccccc1F)N1CCOc2c(N3CCNCC3)cccc21] |
| 27 | 4-(3-Fluoro-benzenesulfonyl)-8-piperazin-1-yl-3,4-dihydro-2H-benzo[1,4]oxazine | 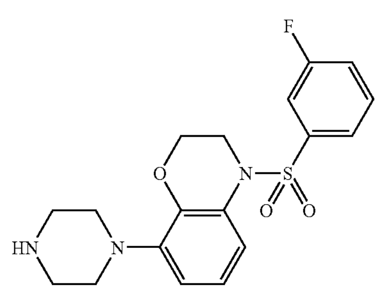 [SMILES: O=S(=O)(c1cccc(F)c1)N1CCOc2c(N3CCNCC3)cccc21] |

TABLE 1-continued

| No. | Name (Autonom ®) |
|---|---|
| 28 | 4-Benzenesulfonyl-6-chloro-8-piperazin-1-yl-3,4-dihydro-2H-benzo[1,4]oxazine |
| 29 | 6-Chloro-4-(2-fluoro-benzenesulfonyl)-8-piperazin-1-yl-3,4-dihydro-2H-benzo[1,4]oxazine |
| 30 | 6-Chloro-4-(naphthalene-1-sulfonyl)-8-piperazin-1-yl-3,4-dihydro-2H-benzo[1,4]oxazine |
| 31 | 4-(2,3-Dichloro-benzenesulfonyl)-8-piperazin-1-yl-3,4-dihydro-2H-benzo[1,4]oxazine |
| 32 | 6-Chloro-8-piperazin-1-yl-4-(thiophene-2-sulfonyl)-3,4-dihydro-2H-benzo[1,4]oxazine |
| 33 | 6-Chloro-8-piperazin-1-yl-4-(quinoline-8-sulfonyl)-3,4-dihydro-2H-benzo[1,4]oxazine |
| 34 | 6-Chloro-4-(3-fluoro-benzenesulfonyl)-8-piperazin-1-yl-3,4-dihydro-2H-benzo[1,4]oxazine |

TABLE 1-continued

| No. | Name (Autonom ®) | Structure |
|-----|------------------|-----------|
| 35 | 6-Chloro-4-(2,4-difluoro-benzenesulfonyl)-8-piperazin-1-yl-3,4-dihydro-2H-benzo[1,4]oxazine | 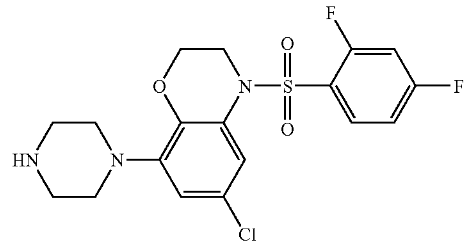 [SMILES: O=S(=O)(c1ccc(F)cc1F)N1CCOc2c(N3CCNCC3)cc(Cl)cc21] |
| 36 | 6-Chloro-4-(5-chloro-thiophene-2-sulfonyl)-8-piperazin-1-yl-3,4-dihydro-2H-benzo[1,4]oxazine | 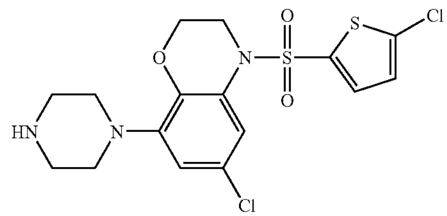 [SMILES: O=S(=O)(c1ccc(Cl)s1)N1CCOc2c(N3CCNCC3)cc(Cl)cc21] |
| 37 | 6-Chloro-4-(3-chloro-benzenesulfonyl)-8-piperazin-1-yl-3,4-dihydro-2H-benzo[1,4]oxazine | 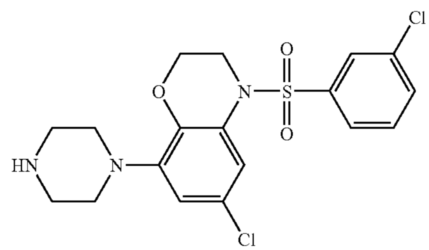 [SMILES: O=S(=O)(c1cccc(Cl)c1)N1CCOc2c(N3CCNCC3)cc(Cl)cc21] |
| 38 | 6-Chloro-4-(2,3-dichloro-benzenesulfonyl)-8-piperazin-1-yl-3,4-dihydro-2H-benzo[1,4]oxazine | 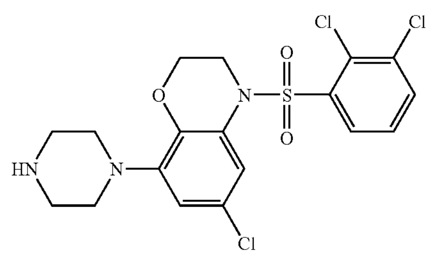 [SMILES: O=S(=O)(c1cccc(Cl)c1Cl)N1CCOc2c(N3CCNCC3)cc(Cl)cc21] |
| 39 | 2-(6-Chloro-8-piperazin-1-yl-2,3-dihydro-benzo[1,4]oxazine-4-sulfonyl)-benzonitrile | 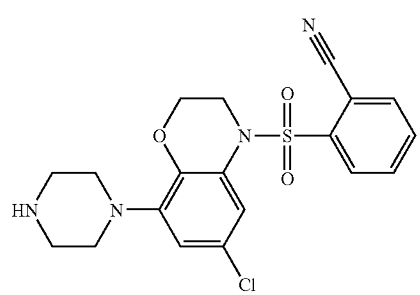 [SMILES: N#Cc1ccccc1S(=O)(=O)N1CCOc2c(N3CCNCC3)cc(Cl)cc21] |
| 40 | 6-Chloro-4-(2-chloro-4-fluoro-benzenesulfonyl)-8-piperazin-1-yl-3,4-dihydro-2H-benzo[1,4]oxazine | 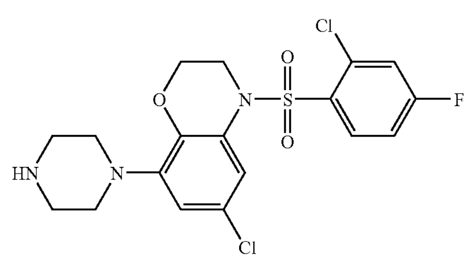 |

TABLE 1-continued

| No. | Name (Autonom ®) |
|---|---|
| 41 | 6-Chloro-4-(5-fluoro-2-methyl-benzenesulfonyl)-8-piperazin-1-yl-3,4-dihydro-2H-benzo[1,4]oxazine |
| 42 | 6-Chloro-4-(5-chloro-naphthalene-1-sulfonyl)-8-piperazin-1-yl-3,4-dihydro-2H-benzo[1,4]oxazine |
| 43 | 6-Chloro-4-(isoquinoline-5-sulfonyl)-8-piperazin-1-yl-3,4-dihydro-2H-benzo[1,4]oxazine |
| 44 | 4-(Benzo[1,2,5]thiadiazole-4-sulfonyl)-6-chloro-8-piperazin-1-yl-3,4-dihydro-2H-benzo[1,4]oxazine |
| 45 | 6-Chloro-4-(1-methyl-1H-imidazole-4-sulfonyl)-8-piperazin-1-yl-3,4-dihydro-2H-benzo[1,4]oxazine |
| 46 | 4-(Benzo[1,2,5]oxadiazole-4-sulfonyl)-6-chloro-8-piperazin-1-yl-3,4-dihydro-2H-benzo[1,4]oxazine |
| 47 | 4-(2-Fluoro-benzenesulfonyl)-6-methyl-8-piperazin-1-yl-3,4-dihydro-2H-benzo[1,4]oxazine |

TABLE 1-continued

| No. | Name (Autonom ®) | Structure |
|---|---|---|
| 48 | 2-(6-Methyl-8-piperazin-1-yl-2,3-dihydro-benzo[1,4]oxazine-4-sulfonyl)-benzonitrile | 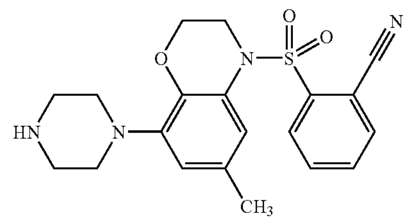 [SMILES: Cc1cc(N2CCNCC2)c2c(c1)N(S(=O)(=O)c1ccccc1C#N)CCO2] |
| 49 | 6-Methyl-8-piperazin-1-yl-4-(thiophene-2-sulfonyl)-3,4-dihydro-2H-benzo[1,4]oxazine | 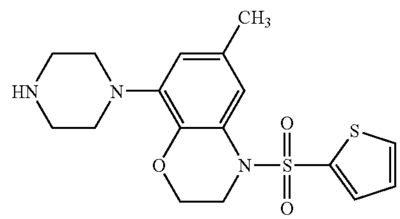 [SMILES: Cc1cc(N2CCNCC2)c2c(c1)N(S(=O)(=O)c1cccs1)CCO2] |
| 50 | 6-Methyl-8-piperazin-1-yl-4-(quinoline-8-sulfonyl)-3,4-dihydro-2H-benzo[1,4]oxazine | 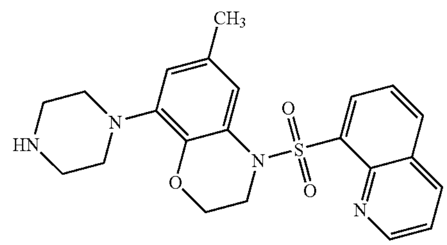 [SMILES: Cc1cc(N2CCNCC2)c2c(c1)N(S(=O)(=O)c1cccc3cccnc13)CCO2] |
| 51 | 4-(3-Fluoro-benzenesulfonyl)-6-methyl-8-piperazin-1-yl-3,4-dihydro-2H-benzo[1,4]oxazine | 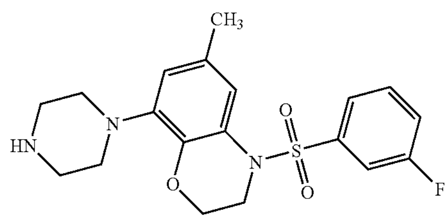 [SMILES: Cc1cc(N2CCNCC2)c2c(c1)N(S(=O)(=O)c1cccc(F)c1)CCO2] |
| 52 | 4-(2,4-Difluoro-benzenesulfonyl)-6-methyl-8-piperazin-1-yl-3,4-dihydro-2H-benzo[1,4]oxazine | 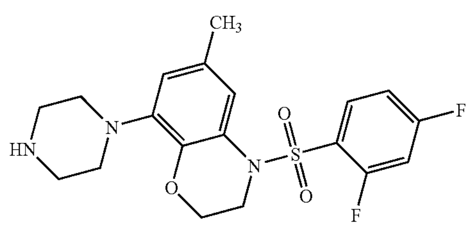 [SMILES: Cc1cc(N2CCNCC2)c2c(c1)N(S(=O)(=O)c1ccc(F)cc1F)CCO2] |
| 53 | 4-(2-Chloro-4-fluoro-benzenesulfonyl)-6-methyl-8-piperazin-1-yl-3,4-dihydro-2H-benzo[1,4]oxazine | 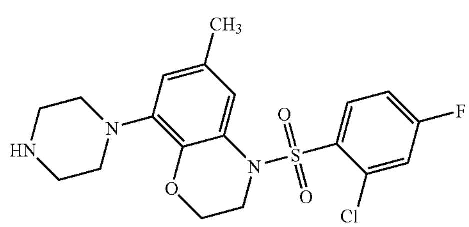 [SMILES: Cc1cc(N2CCNCC2)c2c(c1)N(S(=O)(=O)c1ccc(F)cc1Cl)CCO2] |

TABLE 1-continued

| No. | Name (Autonom ®) | Structure |
|---|---|---|
| 54 | 4-(5-Fluoro-2-methyl-benzenesulfonyl)-6-methyl-8-piperazin-1-yl-3,4-dihydro-2H-benzo[1,4]oxazine | 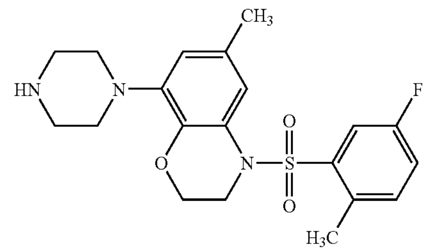 [SMILES: Cc1cc(N2CCNCC2)c2c(c1)N(S(=O)(=O)c1cc(F)ccc1C)CCO2] |
| 55 | 4-(Isoquinoline-5-sulfonyl)-6-methyl-8-piperazin-1-yl-3,4-dihydro-2H-benzo[1,4]oxazine | 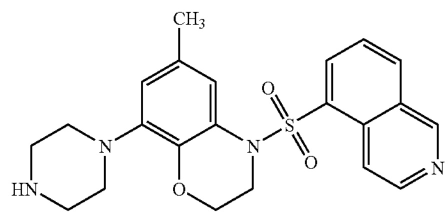 [SMILES: Cc1cc(N2CCNCC2)c2c(c1)N(S(=O)(=O)c1cccc3cnccc13)CCO2] |
| 56 | 6-Methyl-4-(1-methyl-1H-imidazole-4-sulfonyl)-8-piperazin-1-yl-3,4-dihydro-2H-benzo[1,4]oxazine | 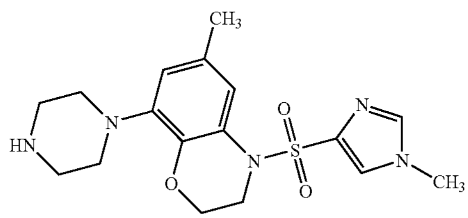 [SMILES: Cc1cc(N2CCNCC2)c2c(c1)N(S(=O)(=O)c1cn(C)cn1)CCO2] |
| 57 | 4-(2-Fluoro-benzenesulfonyl)-6-methoxy-8-piperazin-1-yl-3,4-dihydro-2H-benzo[1,4]oxazine | 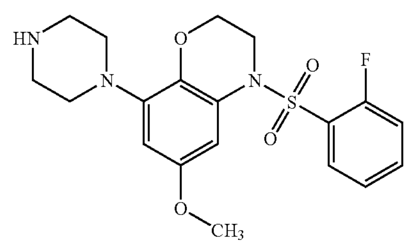 [SMILES: COc1cc(N2CCNCC2)c2c(c1)N(S(=O)(=O)c1ccccc1F)CCO2] |
| 58 | 6-Chloro-4-(2-fluoro-benzenesulfonyl)-8-(4-methyl-piperazin-1-yl)-3,4-dihydro-2H-benzo[1,4]oxazine | 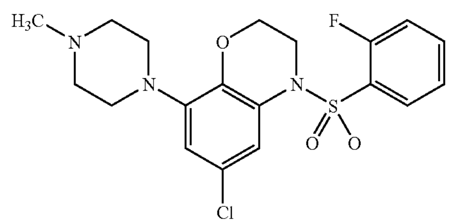 |
| 59 | 6-Fluoro-4-(2-fluoro-benzenesulfonyl)-8-piperazin-1-yl-3,4-dihydro-2H-benzo[1,4]oxazine | 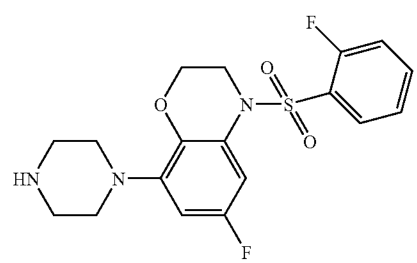 [SMILES: O=S(=O)(c1ccccc1F)N1CCOc2c(N3CCNCC3)cc(F)cc21] |
| 60 | 4-(3-Methanesulfonyl-benzenesulfonyl)-8-(4-methyl-piperazin-1-yl)-3,4-dihydro-2H-benzo[1,4]oxazine | 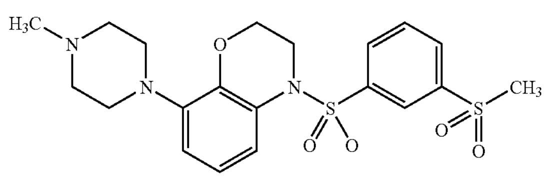 |

TABLE 1-continued

| No. | Name (Autonom ®) | Structure |
|---|---|---|
| 61 | 6-Chloro-8-(4-methyl-piperazin-1-yl)-4-(naphthalene-2-sulfonyl)-3,4-dihydro-2H-benzo[1,4]oxazine | 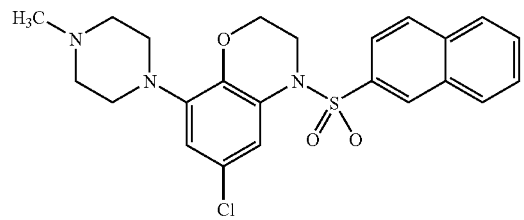 |
| 62 | 4-Benzenesulfonyl-8-(4-methyl-piperazin-1-yl)-3,4-dihydro-2H-benzo[1,4]oxazine | 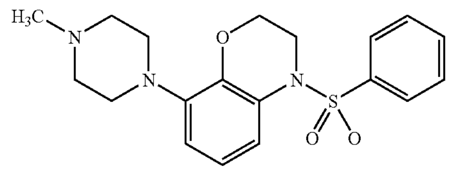 |
| 63 | 4-(2-Fluoro-benzenesulfonyl)-8-(4-methyl-piperazin-1-yl)-3,4-dihydro-2H-benzo[1,4]oxazine | 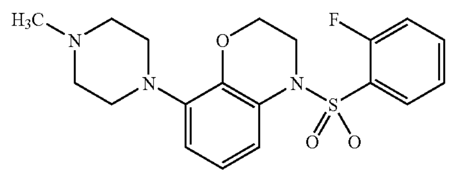 |
| 64 | 4-Benzenesulfonyl-6-methoxy-8-piperazin-1-yl-3,4-dihydro-2H-benzo[1,4]oxazine | 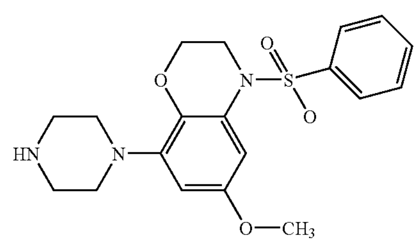 |
| 65 | 4-Benzenesulfonyl-6-fluoro-8-piperazin-1-yl-3,4-dihydro-2H-benzo[1,4]oxazine | 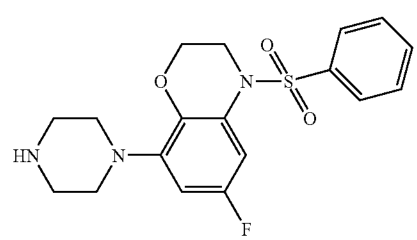 [SMILES: O=S(=O)(c1ccccc1)N1CCOc2c(N3CCNCC3)cc(F)cc21] |
| 66 | 2-(8-Piperazin-1-yl-2,3-dihydro-benzo[1,4]oxazine-4-sulfonyl)-phenol | 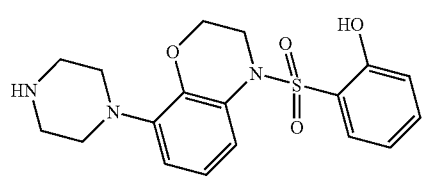 [SMILES: O=S(=O)(c1ccccc1O)N1CCOc2c(N3CCNCC3)cccc21] |
| 67 | 4-(2-Methoxy-benzenesulfonyl)-8-piperazin-1-yl-3,4-dihydro-2H-benzo[1,4]oxazine | 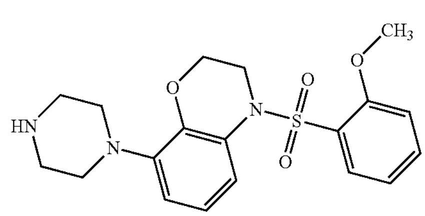 [SMILES: COc1ccccc1S(=O)(=O)N1CCOc2c(N3CCNCC3)cccc21] |

TABLE 1-continued

| No. | Name (Autonom ®) |
|---|---|
| 68 | 4-(2,3-Dihydro-benzo[1,4]dioxine-6-sulfonyl)-6-methoxy-8-piperazin-1-yl-3,4-dihydro-2H-benzo[1,4]oxazine |
| 69 | 4-(2,3-Dihydro-benzo[1,4]dioxine-6-sulfonyl)-6-fluoro-8-piperazin-1-yl-3,4-dihydro-2H-benzo[1,4]oxazine |
| 70 | 6-Methoxy-4-(naphthalene-1-sulfonyl)-8-piperazin-1-yl-3,4-dihydro-2H-benzo[1,4]oxazine |
| 71 | 4-(2-Chloro-benzenesulfonyl)-6-methoxy-8-piperazin-1-yl-3,4-dihydro-2H-benzo[1,4]oxazine |
| 72 | 4-(3-Chloro-benzenesulfonyl)-6-methoxy-8-piperazin-1-yl-3,4-dihydro-2H-benzo[1,4]oxazine |
| 73 | 4-(5-Fluoro-2-methyl-benzenesulfonyl)-6-methoxy-8-piperazin-1-yl-3,4-dihydro-2H-benzo[1,4]oxazine |

TABLE 1-continued

| No. | Name (Autonom ®) | Structure |
|---|---|---|
| 74 | 6-Methoxy-8-piperazin-1-yl-4-(toluene-2-sulfonyl)-3,4-dihydro-2H-benzo[1,4]oxazine | 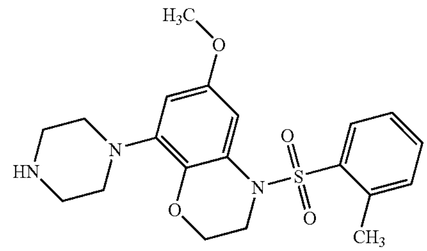 [SMILES: COc1cc(N2CCNCC2)c2c(c1)N(S(=O)(=O)c1ccccc1C)CCO2] |
| 75 | 2-(6-Methyl-8-piperazin-1-yl-2,3-dihydro-benzo[1,4]oxazine-4-sulfonyl)-phenol | 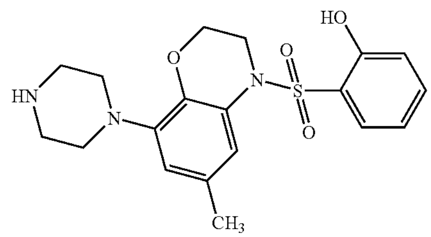 [SMILES: Cc1cc(N2CCNCC2)c2c(c1)N(S(=O)(=O)c1ccccc1O)CCO2] |
| 76 | 6-tert-Butyl-4-(2-fluoro-benzenesulfonyl)-8-piperazin-1-yl-3,4-dihydro-2H-benzo[1,4]oxazine | 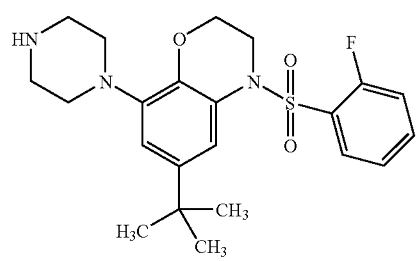 [SMILES: CC(C)(C)c1cc(N2CCNCC2)c2c(c1)N(S(=O)(=O)c1ccccc1F)CCO2] |
| 77 | 6-Piperazin-1-yl-4-(4-piperazin-1-yl-benzenesulfonyl)-3,4-dihydro-2H-benzo[1,4]oxazine | 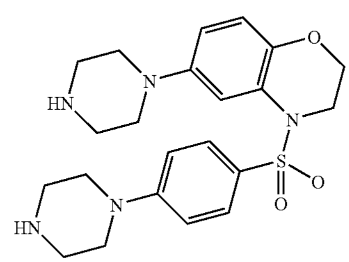 |
| 78 | 4-(3-Chloro-benzenesulfonyl)-8-[1,4]diazepan-1-yl-3,4-dihydro-2H-benzo[1,4]oxazine | 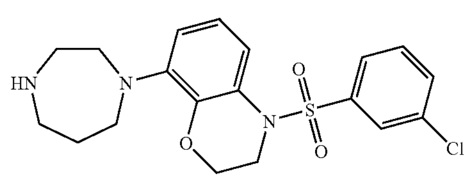 [SMILES: O=S(=O)(c1cccc(Cl)c1)N1CCOc2c(N3CCCNCC3)cccc21] |
| 79 | 4-(2-Fluoro-benzenesulfonyl)-2,2-dimethyl-8-piperazin-1-yl-3,4-dihydro-2H-benzo[1,4]oxazine | 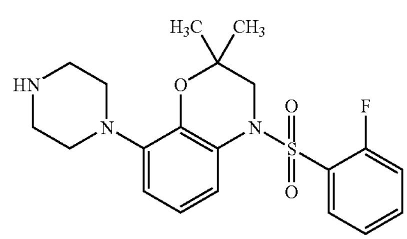 [SMILES: CC1(C)CN(S(=O)(=O)c2ccccc2F)c2cccc(N3CCNCC3)c2O1] |

TABLE 1-continued

| No. | Name (Autonom ®) | Structure |
|-----|------------------|-----------|
| 80 | 9-Benzenesulfonyl-4-piperazin-1-yl-6,7,8,9-tetrahydro-5-oxa-9-aza-benzocycloheptene | 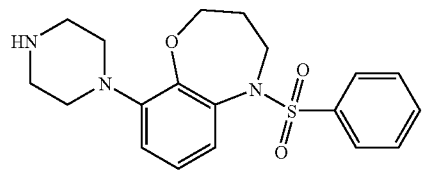 [SMILES: O=S(=O)(c1ccccc1)N1CCCOc2c(N3CCNCC3)cccc21] |

Another aspect of the present invention provides a composition comprising a therapeutically effective amount of a Compound of Formula I and a pharmaceutically acceptable carrier.

Yet another aspect of the present invention provides a method for treating a CNS disease state in a subject comprising administering to the subject a therapeutically effective amount of a Compound of Formula I. Preferably, the disease state comprises psychoses, schizophrenia, manic depressions, neurological disorders, memory disorders, attention deficit disorder, Parkinson's disease, amyotrophic lateral sclerosis, Alzheimer's disease and Huntington's disease.

Still another aspect of the present invention provides a method for treating a disorder of the gastrointestinal tract in a subject comprising administering to the subject a therapeutically effective amount of a Compound of Formula I.

Another aspect of the present invention provides a method for producing a Compound of Formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In one embodiment, Compounds of Formula I, where $Z^1$ is N, are prepared by a coupling reaction between an aryl halide of the formula:

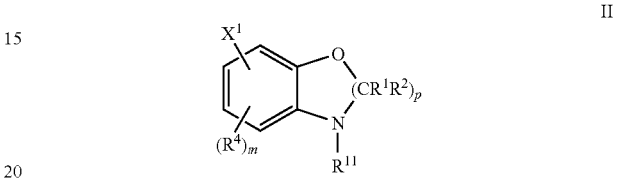

and a heterocyclyl of the formula:

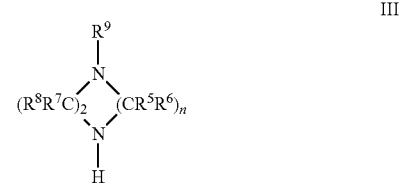

to produce a heterocyclyl-substituted phenyl of the formula:

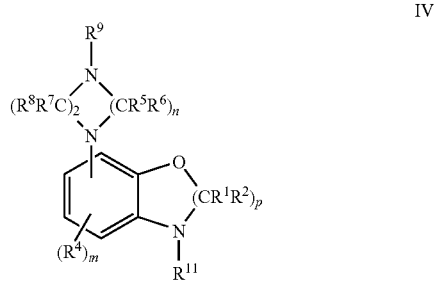

where $R^1$, $R^2$, $R^4$, $R^5$, $R^6$, $R^7$, $R^8$, $R^9$, m, n, and p are those defined herein; $X^1$ is a halide, preferably bromide; and $R^{11}$ is a nitrogen protecting group, or —Y—$R^3$ (where Y and $R^3$ are those defined herein).

The coupling reaction between Compound of Formulas II and III is typically conducted in an inert organic solvent, such as toluene or xylene, in the presence of a coupling catalyst. Suitable coupling catalysts include a mixture of a transition metal catalyst, such as a palladium source (e.g., tris(dibenzylideneacetone)palladium(0) and palladium acetate), and a suitable phosphine ligand, such as 2,2'-bis(diphenylphosphino)-1,1'-binaphthyl, and tri-o-tolylphosphine. In some cases, a base is also added to the coupling reaction. Suitable bases include non-nucleophilic or sterically hindered bases, such as carbonates, bicarbonates, and metal tert-butoxides (e.g., sodium tert-butoxide and potassium tert-butoxide).

The coupling reaction between Compound of Formulas II and III generally requires elevated temperature, typically in the range of from about 50° C. to about 150° C. Preferably, the coupling reaction temperature range is from about 80° C. to about 110° C. More preferably, about 95° C. However, it should be appreciated that the coupling reaction temperature is not limited to these ranges. The coupling reaction temperature can vary significantly depending on the nature of the substrate as well as other factors, such as the coupling catalyst, concentrations of each components, etc.

The reaction time for coupling Compound of Formulas II and III can also vary widely depending on a variety of factors, such as those mentioned above. Generally, the coupling reaction time ranges from about 5 hours to 72 hours, preferably from about 8 hours to about 15 hours, with about 12 hours being a typical coupling reaction time.

After the coupling reaction, the protecting group $R^{11}$ of Compound of Formula IV is removed using conventional deprotection reaction conditions to produce a deprotected heterocyclyl-substituted phenyl of the formula:

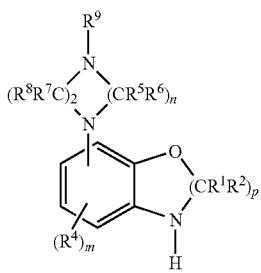

V

Conditions for deprotecting Compound of Formula IV vary depending on the nature of the protecting group $R^{11}$. Suitable deprotection reaction conditions are well known to one skilled in the art. See, for example, *Protective Groups in Organic Synthesis*, 3$^{rd}$ edition, T. W. Greene and P. G. M. Wuts, John Wiley & Sons, New York, 1999, which is incorporated herein by reference in its entirety.

The deprotected heterocyclyl-substituted phenyl of Formula V is then coupled with a compound of the formula: $R^3$—Y—W, wherein W is an activating group, to produce the Compound of Formula I. Suitable activating groups, W, are well known to one skilled in the art. For example, when W is a sulfonyl group (SO$_2$), typical activating groups include halides, preferably chloride.

Coupling conditions for reacting the deprotected heterocyclyl-substituted phenyl of Formula V with the compound of the formula $R^3$—Y—W can include a base. Suitable bases include weakly nucleophilic or non-nucleophilic bases, such as carbonates, bicarbonates, pyridine, and sterically hindered tertiary amine, and other bases known to one skilled in the art.

The reaction temperature ranges widely depending on a variety of factors including the reactivity of reagents. Generally, the coupling reaction temperature ranges from −78° C. to room temperature. Preferably, from −78° C. to about 0° C.

Alternatively, Compounds of Formula I can be prepared by reacting a halogenated aryl of the formula:

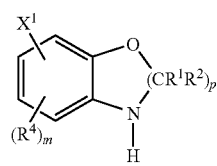

VI with a compound of the formula: $R^3$—Y—W to produce a halogenated phenyl compound of the formula:

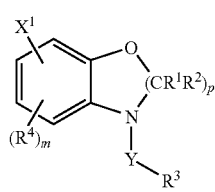

VII

Reaction conditions for coupling the Compound of Formula VI with the Compound of Formula $R^3$—Y—W are similar to those described above for coupling Compound of Formula V with the same activated coupling reagent.

The resulting halogenated phenyl Compound of Formula VII is then coupled with a heterocyclyl compound of the formula:

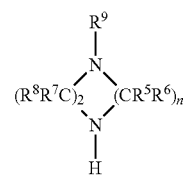

VIII in the presence of a coupling catalyst to produce the Compound of Formula I. Such reaction conditions are similar to those described above for coupling the Compound of Formula II with the Compound of Formula III.

More specific details for producing Compounds of Formula I are described in the Examples section.

Utility

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder.

Testing

The pharmacology of the compounds of this invention was determined by art recognised procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6-12.

EXAMPLES

The following preparations and examples are given to enable those skilled in the art to more clearly understand and to practice the present invention. They should not be considered as limiting the scope of the invention, but merely as being illustrative and representative thereof.

Example 1

This example illustrates a method for producing Compounds of Formula I using the synthetic scheme outlined below:

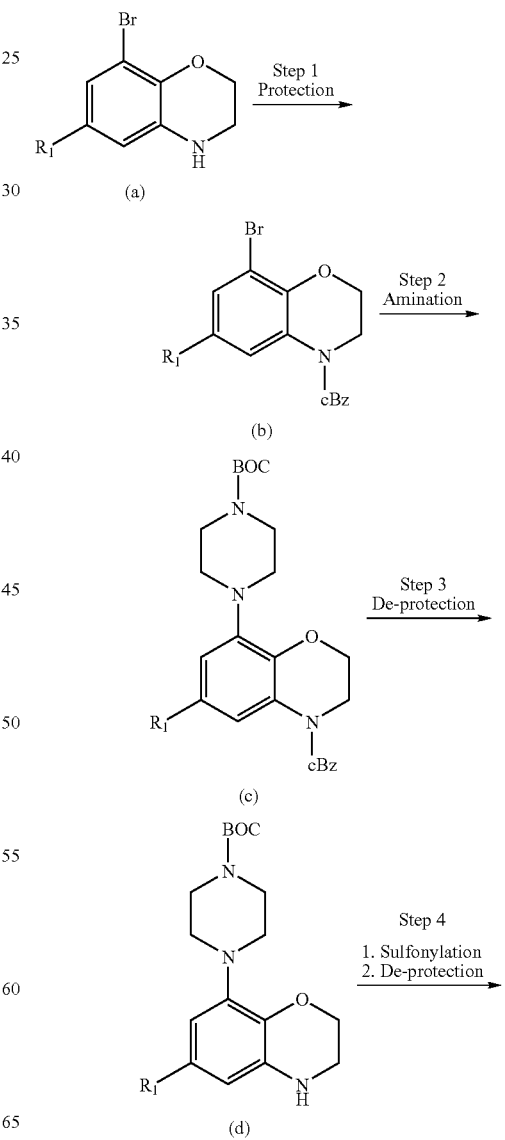

41

-continued

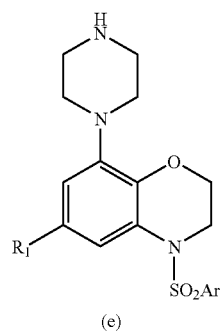

(e)

R₁ = H; Cl; CH₃

Step 1

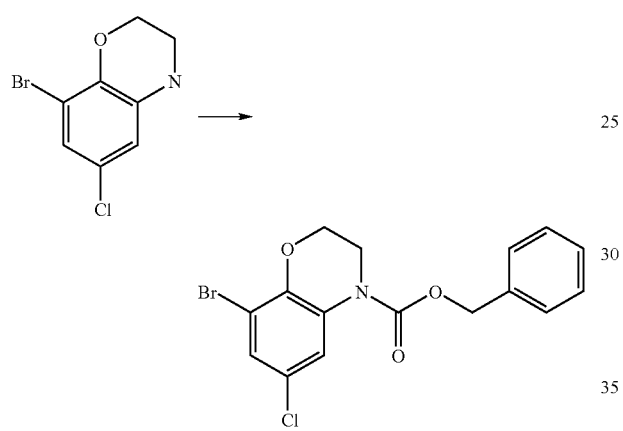

Method A: Synthesis of 8-bromo-6-chloro-2,3-dihydro-benzo[1,4]oxazine-4-carboxylic Acid Benzyl Ester 8-Bromo-6-chloro-2,3-dihydro-benzo[1,4]oxazine used in this Example was prepared by first reacting 2-amino-6-bromo-4-chloro-phenol with chloroacetyl chloride to provide 8-bromo-6-chloro-4H-benzo[1,4]oxazin-3-one using the procedure reported by Combs et al.; J. Med. Chem.; 33; 380-386 1990. This benzoxazinone was then reduced to 8-bromo-6-chloro-2,3-dihydro-benzo[1,4]oxazine using borane in THF according to the procedure described in Tetrahedron; 53(26); 8853-8870 1997.

Benzyl chloroformate (1.877 g, 0.011 mol) was added dropwise to a solution of 8-bromo-6-chloro-3,4-dihydro-2H-benzo[1,4]oxazine (2.85 g, 0.01 mol) in a 1:1 mixture of ethyl acetate (30 mL) and 10% aqueous sodium hydroxide (30 mL). After 3 hours at ambient temperature, the layers were separated and the organic phase was washed with water (2×50 mL), saturated aqueous sodium bicarbonate (50 mL), dried (K₂CO₃) and concentrated in vacuo and the residue was purified by column chromatography on silica gel (eluting with hexane-ethyl acetate; 7:3, V/V) to give 8-bromo-6-chloro-2,3-dihydro-benzo[1,4]oxazine-4-carboxylic acid benzyl ester as an oil (3.47 g, 98%). A sample was recrystallized from ethanol-water. MS: MH⁺ 383. M.P. 95.0-97.7° C.

42

Similarly prepared were:

8-bromo-2,3-dihydro-benzo[1,4]oxazine-4-carboxylic acid benzyl ester (81%);

8-bromo-6-methoxy-2,3-dihydro-benzo[1,4]oxazine-4-carboxylic acid benzyl ester;

8-bromo-6-fluoro-2,3-dihydro-benzo[1,4]oxazine-4-carboxylic acid benzyl ester; and 8-bromo-6-tert-butyl-2,3-dihydro-benzo[1,4]oxazine-4-carboxylic acid benzyl ester

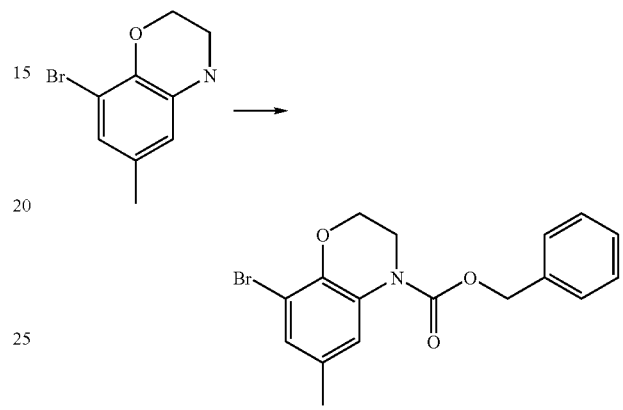

Method B: Synthesis of 8-bromo-6-methyl-2,3-dihydro-benzo[1,4]oxazine-4-carboxylic Acid Benzyl Ester A solution of benzyl chloroformate (1.32 g, 0.008 mol) in dichloromethane (20 mL) was added dropwise under nitrogen to an ice-cold solution of 8-bromo-6-methyl-3,4-dihydro-2H-benzo[1,4]oxazine (1.78 g, 0.007 mol) and pyridine (1.06 g, 0.013 mol) in dichlormethane (40 mL). After 1 hour at ambient temperature, a 10% aqueous HCl solution was added. The layers were separated and the organic phase was washed with water (50 mL×2), dried (Na₂SO₄) and concentrated to give 8-bromo-6-methyl-2,3-dihydro-benzo[1,4]oxazine-4-carboxylic acid benzyl ester as a colorless oil (2.34 g, 96%) which was used in the step 2 without purification.

Step 2

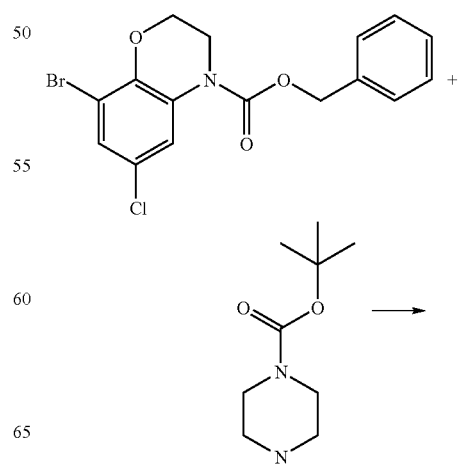

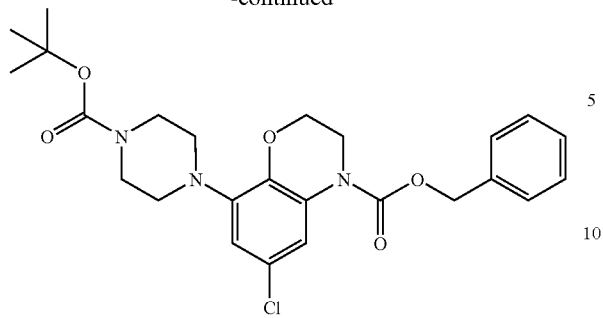

Synthesis of 8-(4-tert-butoxycarbonyl-piperazin-1-yl)-6-chloro-2,3-dihydro-benzo[1,4]oxazine-4-carboxylic Acid A three neck flask was charge with tris(dibenzylideneacetone)dipalladium(0) (21.5 mg, 0.024 mmol, 2 mol % Pd), (±)-2,2'-bis(diphenylphosphino)-1,1'-binaphthyl (36.4 mg, 0.059 mmol, 5 mol %) and sodium-tert-butoxide (159 mg, 1.65 mmol) and flushed with nitrogen. A solution of 8-bromo-6-chloro-2,3-dihydro-benzo[1,4]oxazine-4-carboxylic acid benzyl ester (450 mmg, 1.18 mmol) and piperazine-1-carboxylic acid tert-butyl ester (263 mg, 1.41 mmol) in toluene (2 mL) was added. The mixture was heated to 95° C. and was stirred for 12 hours. The mixture was cooled to room temperature, taken up in ethyl acetate, filtered through celite and concentrated. The crude material was purified by flash chromatography on silica gel (eluting with hexane-ethyl acetate; 7:3, v/v) to give 8-(4-tert-butoxycarbonyl-piperazin-1-yl)-6-chloro-2,3-dihydro-benzo[1,4]oxazine-4-carboxylic acid benzyl ester a colorless oil (275 mg, 48%). MS: MH$^+$=488.

Similarly, using the appropriately substituted methyl-3,4-dihydro-2H-benzo[1,4]oxazine the following compounds were prepared.

8-(4-tert-Butoxycarbonyl-piperazin-1-yl)-2,3-dihydro-benzo[1,4]oxazine-4-carboxylic acid benzyl ester (66%);

8-(4-tert-Butoxycarbonyl-piperazin-1-yl)-6-methyl-2,3-dihydro-benzo[1,4]oxazine-4-carboxylic acid benzyl ester (58%);

8-(4-tert-Butoxycarbonyl-piperazin-1-yl)-6-methoxy-2,3-dihydro-benzo[1,4]oxazine-4-carboxylic acid benzyl ester;

8-(4-tert-Butoxycarbonyl-piperazin-1-yl)-6-fluoro-2,3-dihydro-benzo[1,4]oxazine-4-carboxylic acid benzyl ester; and 8-(4-tert-Butoxycarbonyl-piperazin-1-yl)-6-tert-butyl-2,3-dihydro-benzo[1,4]oxazine-4-carboxylic acid benzyl ester.

Step 3

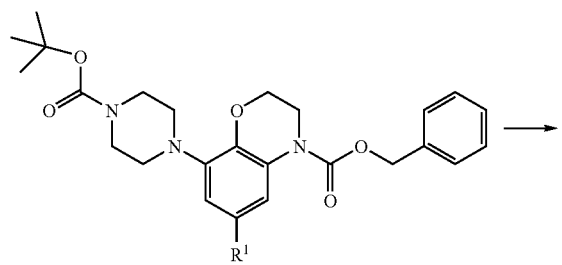

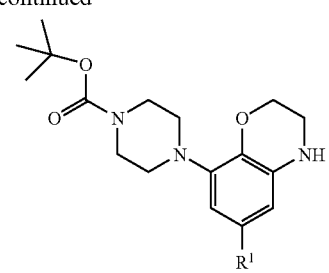

$R^1$ = Cl, H

Method A: Synthesis of 4-(6-chloro-3,4-dihydro-2H-benzo[1,4]oxazin-8-yl)-piperazine-1-carboxylic Acid Tert-Butyl Ester ($R_1$=Cl)

A solution of 8-(4-tert-butoxycarbonyl-piperazin-1-yl)-6-chloro-2,3-dihydro-benzo[1,4]oxazine-4-carboxylic acid benzyl ester (870 mg, 1.79 mmol) in ethanol (10 mL) was hydrogenated at atmospheric pressure over 10% Pd/C (75 mg) for 0.5 hour. The catalyst was removed by filtration, and the filtrate was concentrated. The crude material was purified by flash chromatography on silica gel (eluting with hexane-ethyl acetate; 1:1, v/v) to give 4-(6-chloro-3,4-dihydro-2H-benzo[1,4]oxazin-8-yl)-piperazine-1-carboxylic acid tert-butyl ester as a white foam (450 mg, 71%). MS: MH$^+$=354.

Similarly the following compound was prepared 4-(3,4-Dihydro-2H-benzo[1,4]oxazin-8-yl)-piperazine-1-carboxylic acid tert-butyl ester (95%). MS: MH$^+$ 320.

4-(6-Methyl-3,4-dihydro-2H-benzo[1,4]oxazin-8-yl)-piperazine-1-carboxylic acid tert-butyl ester (95%). MS: MH$^+$ 334.

Method B: Synthesis of 4-(3,4-dihydro-2H-benzo[1,4]oxazin-8-yl)-piperazine-1-carboxylic Acid Tert-Butyl Ester ($R_1$=H)

A solution of 8-(4-tert-butoxycarbonyl-piperazin-1-yl)-6-chloro-2,3-dihydro-benzo[1,4]oxazine-4-carboxylic acid benzyl ester (640 mg, 1.32 mmol) in ethanol (10 mL) was hydrogenated at 50 psi in the presence of palladium on carbon for 12 hours. The catalyst was removed by filtration, and the filtrate was concentrated to give 4-(3,4-dihydro-2H-benzo[1,4]oxazin-8-yl)-piperazine-1-carboxylic acid tert-butyl ester as a light yellow solid (350 mg, 84%). MS: MH$^+$=320.

Similarly prepared were:

4-(6-Methoxy-3,4-dihydro-2H-benzo[1,4]oxazin-8-yl)-piperazine-1-carboxylic acid tert-butyl ester;

4-(6-Fluoro-3,4-dihydro-2H-benzo[1,4]oxazin-8-yl)-piperazine-1-carboxylic acid tert-butyl ester; and 4-(6-tert-Butyl-3,4-dihydro-2H-benzo[1,4]oxazin-8-yl)-piperazine-1-carboxylic acid tert-butyl ester.

Step 4

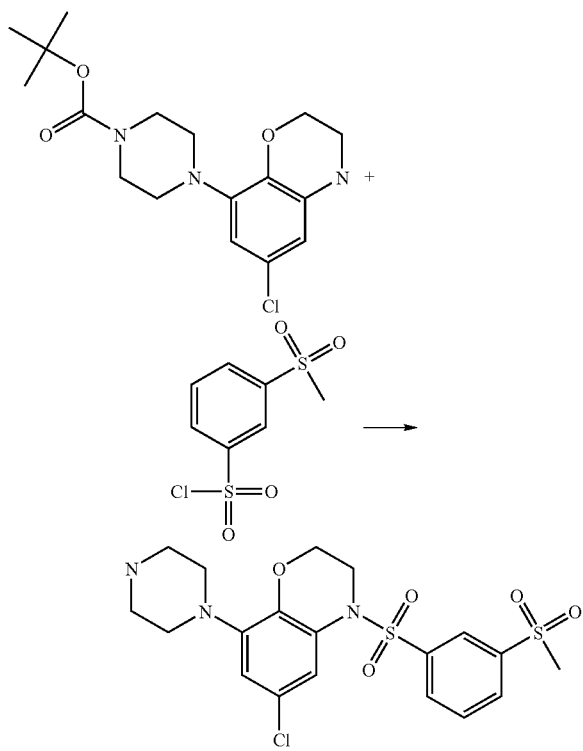

Synthesis of 6-chloro-4-(3-methanesulfonyl-benzenesulfonyl)-8-piperazin-1-yl-3,4-dihydro-2H-benzo[1,4]oxazine 3-Methanesulfonyl-benzenesulfonyl chloride (80 mg, 0.314 mmol) was added in small portions under nitrogen to an ice-cold solution of 4-(6-chloro-3,4-dihydro-2H-benzo[1,4]oxazin-8-yl)-piperazine-1-carboxylic acid tert-butyl ester (101 mg, 0.285 mmol) and pyridine (50 mg, 0.628 mmol) in dichlormethane (2 mL). After 1.5 hours at ambient temperature, water was added. The layers were separated and the organic phase was washed with saturated aqueous solution of sodium bicarbonate (20 mL), dried ($Na_2SO_4$) and concentrated to give 4-[6-chloro-4-(3-methanesulfonyl-benzenesulfonyl)-3,4-dihydro-2H-benzo[1,4]oxazin-8-yl]-piperazine-1-carboxylic acid tert-butyl ester as an oil (150 mg, 91%).

The crude material was dissolved in ethanol (1 mL) and was treated with a solution of 10% hydrogen chloride in ethanol (1 mL). The mixture was heated on a steam bath for 15 minutes. White crystals precipitated upon cooling to ambient temperature. The solid was collected, washed with cold ethanol. Drying under vacuum gave 6-chloro-4-(3-methanesulfonyl-benzenesulfonyl)-8-piperazin-1-yl-3,4-dihydro-2H-benzo[1,4]oxazine, hydrochloride salt as a white powder (130 mg, 95%). MS: $MH^+$=472. M.p. 147.2-153° C.

Similarly, but replacing 3-methylsulfonyl-benzenesulfonyl chloride with the appropriate arylsulfonyl chlorides followed by de-protection using trifluoracetic acid, the following compounds were prepared:

6-Chloro-4-(3-fluoro-benzenesulfonyl)-8-piperazin-1-yl-3,4-dihydro-2H-benzo[1,4]oxazine, trifluoroacetic acid salt. MS: $MH^+$=412.

6-Chloro-4-(2,4-difluoro-benzenesulfonyl)-8-piperazin-1-yl-3,4-dihydro-2H-benzo[1,4]oxazine, trifluoroacetic acid salt. MS: $MH^+$=430.

6-Chloro-4-(3-chloro-benzenesulfonyl)-8-piperazin-1-yl-3,4-dihydro-2H-benzo[1,4]oxazine, trifluoroacetic acid salt. MS: $MH^+$=419.

6-Chloro-4-(2,3-dichloro-benzenesulfonyl)-8-piperazin-1-yl-3,4-dihydro-2H-benzo[1,4]oxazine, trifluoroacetic acid salt. MS: $MH^+$=463.

6-Chloro-4-(2-chloro-3-fluoro-benzenesulfonyl)-8-piperazin-1-yl-3,4-dihydro-2H-benzo[1,4]oxazine, trifluoroacetic acid salt. MS: $MH^+$=447.

6-Chloro-4-(4-fluoro-2-methyl-benzenesulfonyl)-8-piperazin-1-yl-3,4-dihydro-2H-benzo[1,4]oxazine, trifluoroacetic acid salt. MS: $MH^+$=447.

6-Chloro-4-(5-chloro-naphthalene-1-sulfonyl)-8-piperazin-1-yl-3,4-dihydro-2H-benzo[1,4]oxazine, trifluoroacetic acid salt. MS: $MH^+$=479.

6-Chloro-8-piperazin-1-yl-4-(quinoline-8-sulfonyl)-3,4-dihydro-2H-benzo[1,4]oxazine, trifluoroacetic acid salt. MS: $MH^+$=445

6-Chloro-4-(isoquinoline-5-sulfonyl)-8-piperazin-1-yl-3,4-dihydro-2H-benzo[1,4]oxazine, trifluoroacetic acid salt. MS: $MH^+$=445

2-(6-Chloro-8-piperazin-1-yl-2,3-dihydro-benzo[1,4]oxazine-4-sulfonyl)-benzonitrile, trifluoroacetic acid salt. MS: $MH^+$=419.

6-Chloro-8-piperazin-1-yl-4-(thiophene-2-sulfonyl)-3,4-dihydro-2H-benzo[1,4]oxazine, trifluoroacetic acid salt.

4-(Benzo[1,2,5]thiadiazole-4-sulfonyl)-6-chloro-8-piperazin-1-yl-3,4-dihydro-2H-benzo[1,4]oxazine, trifluoroacetic acid salt. MS: $MH^+$=452.

6-Chloro-4-(1-methyl-1H-imidazole-4-sulfonyl)-8-piperazin-1-yl-3,4-dihydro-2H-benzo[1,4]oxazine, trifluoroacetic acid salt. MS: $MH^+$=398.

6-Chloro-4-(5-chloro-thiophene-2-sulfonyl)-8-piperazin-1-yl-3,4-dihydro-2H-benzo[1,4]oxazine, trifluoroacetic acid salt. MS: $MH^+$=435.

4-(Benzo[1,2,5]oxadiazole-4-sulfonyl)-6-chloro-8-piperazin-1-yl-3,4-dihydro-2H-benzo[1,4]oxazine, trifluoroacetic acid salt. MS: $MH^+$=436.

Similarly, but replacing piperazine-1-carboxylic acid tert-butyl ester in step 2 with N-methyl piperazine and using the appropriate aryl- or heteroaryl-chloride in step 4 followed by deprotection with HCl, the following were prepared:

6-Chloro-8-(4-methyl-piperazin-1-yl)-4-(naphthalene-2-sulfonyl)-3,4-dihydro-2H-benzo[1,4]oxazine, hydrochloride salt. MS: $MH^+$=457.

6-Chloro-4-(2-fluoro-benzenesulfonyl)-8-(4-methyl-piperazin-1-yl)-3,4-dihydro-2H-benzo[1,4]oxazine, hydrochloride salt. MS: $MH^+$=425.

Similarly, but replacing 4-(6-chloro-3,4-dihydro-2H-benzo[1,4]oxazin-8-yl)-piperazine-1-carboxylic acid tert-butyl ester with 4-(3,4-dihydro-2H-benzo[1,4]oxazin-8-yl)-piperazine-1-carboxylic acid tert-butyl ester, and replacing 3-methylsulfonyl-benzenesulfonyl chloride with the appropriate aryl- or heteroaryl-sulfonyl chlorides followed by de-protection using trifluoracetic acid or hot hydrogen chloride in ethanol, the following compounds were prepared:

4-(4-Chloro-benzenesulfonyl)-8-piperazin-1-yl-3,4-dihydro-2H-benzo[1,4]oxazine, trifluoroacetic acid salt. MS: $MH^+$=390.

4-(3-Chloro-benzenesulfonyl)-8-piperazin-1-yl-3,4-dihydro-2H-benzo[1,4]oxazine, trifluoroacetic acid salt. MS: $MH^+$=390.

4-(3,4-Dichloro-benzenesulfonyl)-8-piperazin-1-yl-3,4-dihydro-2H-benzo[1,4]oxazine, trifluoroacetic acid salt. MS: MH$^+$=429.

4-(2,3-Dichloro-benzenesulfonyl)-8-piperazin-1-yl-3,4-dihydro-2H-benzo[1,4]oxazine, trifluoroacetic acid salt. MS: MH$^+$=429.

4-(2,6-Dichloro-benzenesulfonyl)-8-piperazin-1-yl-3,4-dihydro-2H-benzo[1,4]oxazine, trifluoroacetic acid salt. MS: MH$^+$=429.

4-(2,4-Dichloro-benzenesulfonyl)-8-piperazin-1-yl-3,4-dihydro-2H-benzo[1,4]oxazine, trifluoroacetic acid salt. MS: MH$^+$=429.

4-(3,5-Dichloro-benzenesulfonyl)-8-piperazin-1-yl-3,4-dihydro-2H-benzo[1,4]oxazine, trifluoroacetic acid salt. MS: MH$^+$=429.

4-(4-Methoxy-benzenesulfonyl)-8-piperazin-1-yl-3,4-dihydro-2H-benzo[1,4]oxazine, trifluoroacetic acid salt. MS: MH$^+$=429.

8-piperazin-1-yl-4-(quinoline-8-sulfonyl)-3,4-dihydro-2H-benzo[1,4]oxazine, trifluoroacetic acid salt. MS: MH$^+$=411.

4-Benzenesulfonyl-8-piperazin-1-yl-3,4-dihydro-2H-benzo[1,4]oxazine, hydrochloride salt as a white powder. MS: MH$^+$=360. M.p. 235.8-239.5° C.

4-(2-Chloro-benzenesulfonyl)-8-piperazin-1-yl-3,4-dihydro-2H-benzo[1,4]oxazine, hydrochloride salt as white powder. MS: MH$^+$=390. M.p. 246.9-248.8° C.

4-(3-Fluoro-benzenesulfonyl)-8-piperazin-1-yl-3,4-dihydro-2H-benzo[1,4]oxazine, hydrochloride salt as a white powder. MS: MH$^+$=378. M.p. 186.6-187.9° C.

4-(2-Fluoro-benzenesulfonyl)-8-piperazin-1-yl-3,4-dihydro-2H-benzo[1,4]oxazine, hydrochloride salt as a white powder. MS: MH$^+$=378. M.p. 258.7-259.4° C.

4-(3-methanesulfonyl-benzenesulfonyl)-8-piperazin-1-yl-3,4-dihydro-2H-benzo[1,4]oxazine, hydrochloride salt as a white powder. MS: MH$^+$=438. M.p. 193.9-203.8° C.

4-(2-methanesulfonyl-benzenesulfonyl)-8-piperazin-1-yl-3,4-dihydro-2H-benzo[1,4]oxazine, hydrochloride salt as a white powder. MS: MH$^+$=438. M.p. 168.7-171.9° C.

4-(2,3-Dichloro-benzenesulfonyl)-8-piperazin-1-yl-3,4-dihydro-2H-benzo[1,4]oxazine, hydrochloride salt as a white powder. MS: MH$^+$=429. M.p. 266.9-271.9° C.

2-(8-piperazin-1-yl-2,3-dihydro-benzo[1,4]oxazine-4-sulfonyl)-phenol, hydrochloride salt. MS: MH$^+$ 374.

4-(2-Methoxy-benzenesulfonyl)-8-piperazin-1-yl-3,4-dihydro-2H-benzo[1,4]oxazine, hydrochloride salt. MS: MH$^+$ 388.

6-piperazin-1-yl-4-(4-piperazin-1-yl-benzenesulfonyl)-3,4-dihydro-2H-benzo[1,4]oxazine, hydrochloride salt. MS: MH$^+$ 443.

Similarly, but replacing 8-bromo-6-chloro-2,3-dihydro-benzo[1,4]oxazine-4-carboxylic acid benzyl ester and piperazine-1-carboxylic acid tert-butyl ester in step 2 respectively with 8-bromo-2,3-dihydro-benzo[1,4]oxazine-4-carboxylic acid benzyl ester and methyl piperazine, and subsequently using the appropriate arylsulfonyl chloride in step 4 followed by deprotection, the following were prepared:

4-(3-Methanesulfonyl-benzenesulfonyl)-8-(4-methyl-piperazin-1-yl)-3,4-dihydro-2H-benzo[1,4]oxazine, hydrochloride salt. MS: MH$^+$ 451.

4-Benzenesulfonyl-8-(4-methyl-piperazin-1-yl)-3,4-dihydro-2H-benzo[1,4]oxazine, hydrochloride salt. MS: MH$^+$ 372.

4-(2-Fluoro-benzenesulfonyl)-8-(4-methyl-piperazin-1-yl)-3,4-dihydro-2H-benzo[1,4]oxazine, hydrochloride salt. MS: MH$^+$ 390.

Similarly, but replacing 4-(6-chloro-3,4-dihydro-2H-benzo[1,4]oxazin-8-yl)-piperazine-1-carboxylic acid tert-butyl ester with 4-(6-methyl-3,4-dihydro-2H-benzo[1,4]oxazin-8-yl)-piperazine-1-carboxylic acid tert-butyl ester, and replacing 3-methylsulfonyl-benzenesulfonyl chloride with the appropriate aryl- or heteroaryl-sulfonyl chlorides followed by de-protection using trifluoracetic acid or hot hydrogen chloride in ethanol, the following compounds were prepared:

4-(2-Fluoro-benzenesulfonyl)-6-methyl-8-piperazin-1-yl-3,4-dihydro-2H-benzo[1,4]oxazine, trifluoroacetic acid salt, MS: MH$^+$ 390.

2-(6-Methyl-8-piperazin-1-yl-2,3-dihydro-benzo[1,4]oxazine-4-sulfonyl)-benzonitrile, trifluoroacetic acid salt, MS: MH$^+$ 397.

6-Methyl-8-piperazin-1-yl-4-(thiophene-2-sulfonyl)-3,4-dihydro-2H-benzo[1,4]oxazine, trifluoroacetic acid salt, MS: MH$^+$ 379.

6-Methyl-8-piperazin-1-yl-4-(quinoline-8-sulfonyl)-3,4-dihydro-2H-benzo[1,4]oxazine, trifluoroacetic acid salt, MS: MH$^+$ 424.

4-(3-Fluoro-benzenesulfonyl)-6-methyl-8-piperazin-1-yl-3,4-dihydro-2H-benzo[1,4]oxazine, trifluoroacetic acid salt, MS: MH$^+$ 390.

4-(2,4-Difluoro-benzenesulfonyl)-6-methyl-8-piperazin-1-yl-3,4-dihydro-2H-benzo[1,4]oxazine, trifluoroacetic acid salt, MS: MH$^+$ 408.

4-(2-Chloro-4-fluoro-benzenesulfonyl)-6-methyl-8-piperazin-1-yl-3,4-dihydro-2H-benzo[1,4]oxazine, trifluoroacetic acid salt, MS: MH$^+$ 425.

4-(5-Fluoro-2-methyl-benzenesulfonyl)-6-methyl-8-piperazin-1-yl-3,4-dihydro-2H-benzo[1,4]oxazine, trifluoroacetic acid salt, MS: MH$^+$ 404.

4-(Isoquinoline-5-sulfonyl)-6-methyl-8-piperazin-1-yl-3,4-dihydro-2H-benzo[1,4]oxazine, trifluoroacetic acid salt, MS: MH$^+$ 424.

6-Methyl-4-(1-methyl-1H-imidazole-4-sulfonyl)-8-piperazin-1-yl-3,4-dihydro-2H-benzo[1,4]oxazine, trifluoroacetic acid salt, MS: MH$^+$ 376.

Similarly, but replacing 4-(6-chloro-3,4-dihydro-2H-benzo[1,4]oxazin-8-yl)-piperazine-1-carboxylic acid tert-butyl ester with 4-(6-methoxy-3,4-dihydro-2H-benzo[1,4]oxazin-8-yl)-piperazine-1-carboxylic acid tert-butyl ester, and replacing 3-methylsulfonyl-benzenesulfonyl chloride with the appropriate aryl- or heteroaryl-sulfonyl chlorides followed by de-protection using trifluoracetic acid or hot hydrogen chloride in ethanol, the following compounds were prepared:

4-(2-Fluoro-benzenesulfonyl)-6-methoxy-8-piperazin-1-yl-3,4-dihydro-2H-benzo[1,4]oxazine, hydrochloride salt, MS: MH$^+$ 406.

4-Benzenesulfonyl-6-methoxy-8-piperazin-1-yl-3,4-dihydro-2H-benzo[1,4]oxazine, hydrochloride salt, MS: MH$^+$ 388.

4-(2,3-Dihydro-benzo[1,4]dioxine-6-sulfonyl)-6-methoxy-8-piperazin-1-yl-3,4-dihydro-2H-benzo[1,4]oxazine, hydrochloride salt, MS: MH$^+$ 447.

6-Methoxy-4-(naphthalene-1-sulfonyl)-8-piperazin-1-yl-3,4-dihydro-2H-benzo[1,4]oxazine, trifluoroacetic acid salt, MS: MH$^+$ 439.

4-(2-Chloro-benzenesulfonyl)-6-methoxy-8-piperazin-1-yl-3,4-dihydro-2H-benzo[1,4]oxazine, trifluoroacetic acid salt, MS: MH$^+$ 423.

4-(3-Chloro-benzenesulfonyl)-6-methoxy-8-piperazin-1-yl-3,4-dihydro-2H-benzo[1,4]oxazine, trifluoroacetic acid salt, MS: MH$^+$ 423.

4-(5-Fluoro-2-methyl-benzenesulfonyl)-6-methoxy-8-piperazin-1-yl-3,4-dihydro-2H-benzo[1,4]oxazine, trifluoroacetic acid salt, MS: MH$^+$ 420.

6-Methoxy-8-piperazin-1-yl-4-(toluene-2-sulfonyl)-3,4-dihydro-2H-benzo[1,4]oxazine, trifluoroacetic acid salt, MS: MH$^+$ 402.

Similarly, but replacing 4-(6-chloro-3,4-dihydro-2H-benzo[1,4]oxazin-8-yl)-piperazine-1-carboxylic acid tert-butyl ester with 4-(6-fluoro-3,4-dihydro-2H-benzo[1,4]oxazin-8-yl)-piperazine-1-carboxylic acid tert-butyl ester, and replacing 3-methylsulfonyl-benzenesulfonyl chloride with the appropriate aryl- or heteroaryl-sulfonyl chlorides followed by de-protection using trifluoracetic acid or hot hydrogen chloride in ethanol, the following compounds were prepared:

6-Fluoro-4-(2-fluoro-benzenesulfonyl)-8-piperazin-1-yl-3,4-dihydro-2H-benzo[1,4]oxazine, hydrochloride salt, MS: MH$^+$ 394.

4-Benzenesulfonyl-6-fluoro-8-piperazin-1-yl-3,4-dihydro-2H-benzo[1,4]oxazine, hydrochloride salt, MS: MH$^+$ 376.

4-(2,3-Dihydro-benzo[1,4]dioxine-6-sulfonyl)-6-fluoro-8-piperazin-1-yl-3,4-dihydro-2H-benzo[1,4]oxazine, hydrochloride salt, MS: MH$^+$ 434.

Similarly, but replacing 4-(6-chloro-3,4-dihydro-2H-benzo[1,4]oxazin-8-yl)-piperazine-1-carboxylic acid tert-butyl ester with 4-(6-tert-butyl-3,4-dihydro-2H-benzo[1,4]oxazin-8-yl)-piperazine-1-carboxylic acid tert-butyl ester, and replacing 3-methylsulfonyl-benzenesulfonyl chloride with the appropriate aryl- or heteroaryl-sulfonyl chlorides followed by de-protection using trifluoracetic acid or hot hydrogen chloride in ethanol, the following was prepared:

6-tert-Butyl-4-(2-fluoro-benzenesulfonyl)-8-piperazin-1-yl-3,4-dihydro-2H-benzo[1,4]oxazine, hydrochloride salt, MS: MH$^+$ 433.

Example 2

Synthesis of N-[3-(8-piperazin-1-yl-2,3-dihydrobenzo[1,4]oxazine-4-sulfonyl)-phenyl]-methanesulfonamide Step 1

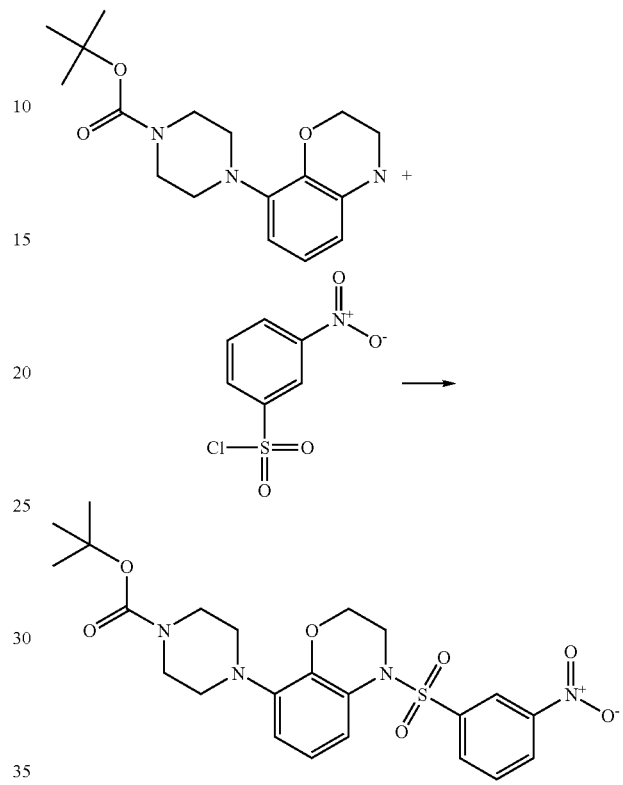

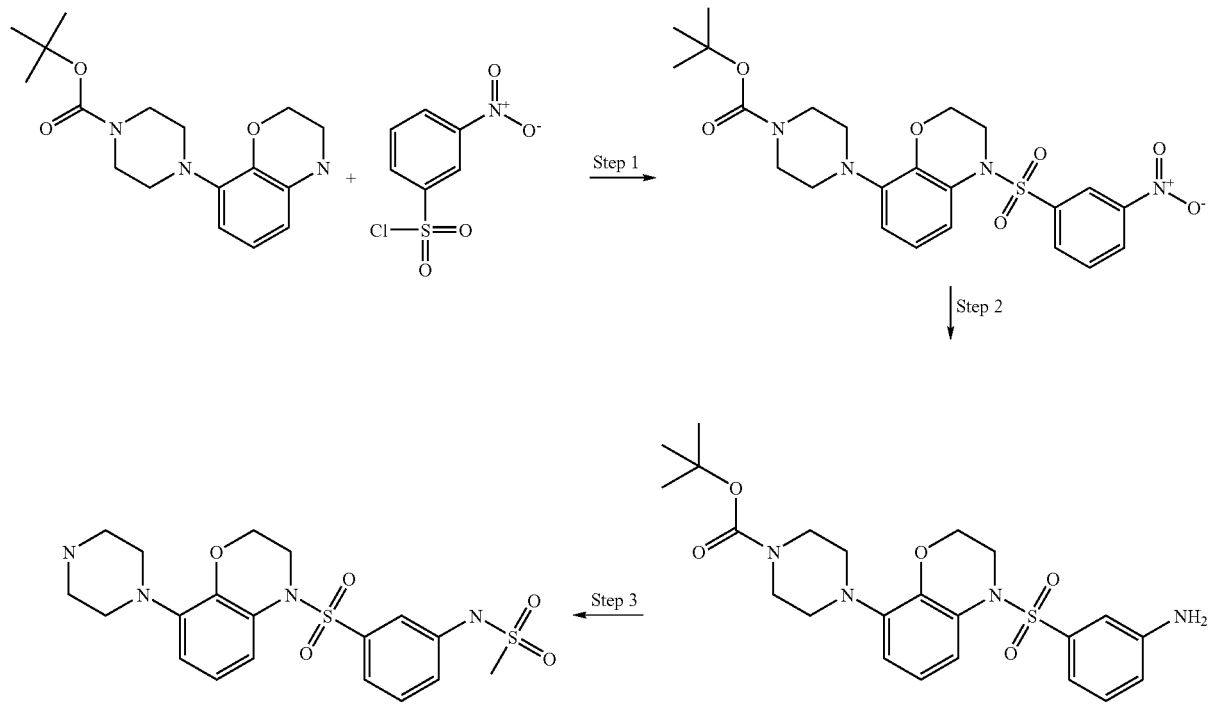

3-Nitro-benzenesulfonyl chloride (122.9 mg, 0.55 mmol) was added in small portions under nitrogen to an ice-cold solution of 4-(3,4-dihydro-2H-benzo[1,4]oxazin-8-yl)-piperazine-1-carboxylic acid tert-butyl ester (161 mg, 0.504 mmol) and pyridine (88 mg, 1.11 mmol) in dichlormethane (2 mL). After 0.5 hour at ambient temperature, water was added. The organic phase was separated, washed with saturated aqueous solution of sodium bicarbonate (20 mL), dried (Na$_2$SO$_4$) and concentrated to give 4-[4-(3-nitro-benzenesulfonyl)-3,4-dihydro-2H-benzo[1,4]oxazin-8-yl]-piperazine-1-carboxylic acid tert-butyl ester as an oil (260 mg). MS: MH$^+$=505.

Step 2

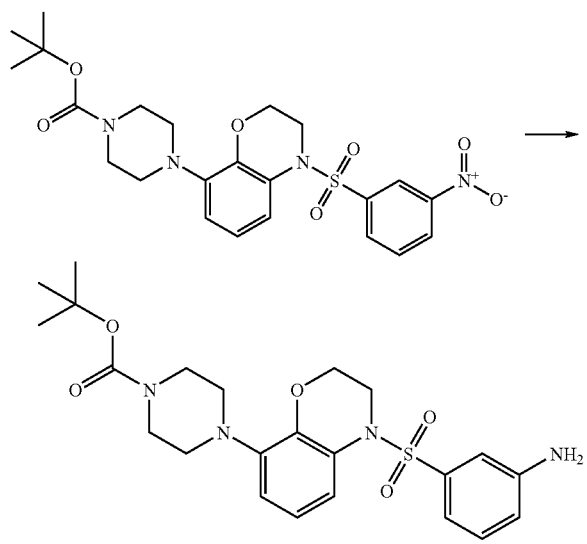

A solution of the crude material from Procedure a in ethanol (5 mL) was hydrogenated at atmospheric pressure over 10% Pd/C (50 mg) for 0.5 hour. The catalyst was removed by filtration, and the filtrate was concentrated to give 4-[4-(3-amino-benzenesulfonyl)-3,4-dihydro-2H-benzo[1,4]oxazin-8-yl]-piperazine-1-carboxylic acid tert-butyl ester as a white solid (150 mg). MS: MH$^+$=475.

Step 3

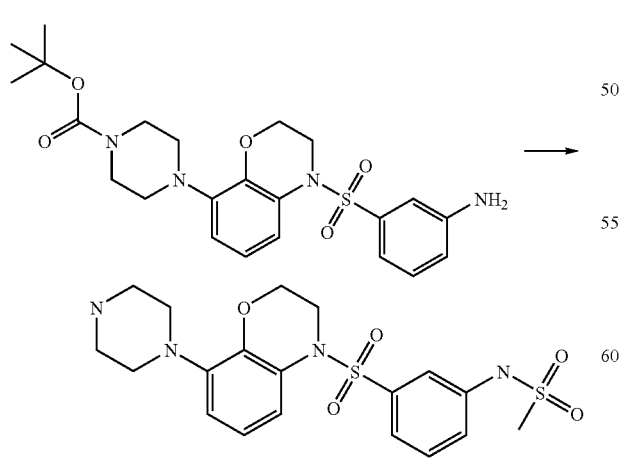

A solution of methanesulfonyl chloride (75 mg, 0.64 mmol) in dichloromethane (0.5 mL) was added dropwise under nitrogen to an ice-cold solution of the crude material obtained in Procedure b (145 mg, 0.31 mmol) and triethylamine (65 mg, 0.65 mmol) in dichloromethane (2 mL). After 1 hour at ambient temperature, water (2 mL) was added. The layers were separated. The organic phase was washed with water (2 mL), dried (Na$_2$SO$_4$) and concentrated to give 4-[4-(3-dimethanesulfonylamino-benzenesulfonyl)-3,4-dihydro-2H-benzo[1,4]oxazin-8-yl]-piperazine-1-carboxylic acid tert-butyl ester as an oil (50 mg, 25%).

A solution of the above intermediate in tetrahydrofuran (1 mL) was treated with 2N sodium hydroxide (1 mL). After 12 hours, ethyl acetate was added (10 mL). The layers were separated, dried (Na$_2$SO$_4$) and concentrated. De-protection as described in step 4 above gave N-[3-(8-piperazin-1-yl-2,3-dihydro-benzo[1,4]oxazine-4-sulfonyl)-phenyl]-methanesulfonamide (25 mg, 30%) as a off-white powder. MS: MH$^+$=453. M.p. 158.5-163.5° C.

Example 3

This example illustrates a method for producing Compounds of Formula I using the synthetic scheme outlined below:

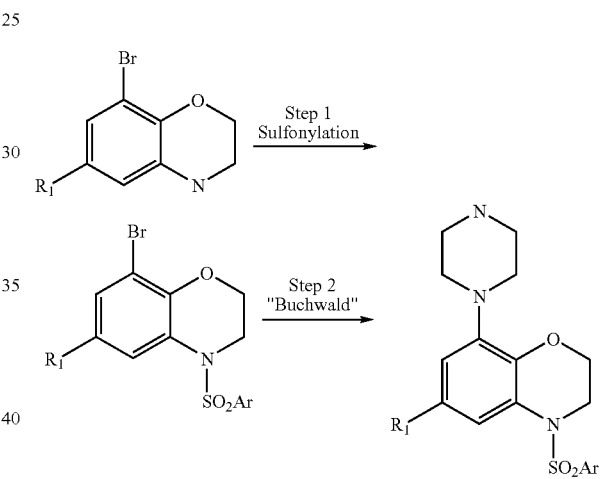

Step 1

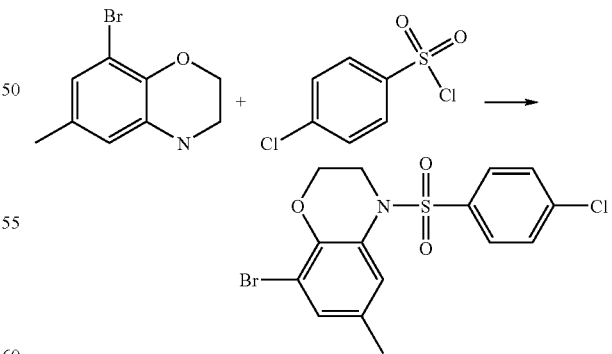

Synthesis of 8-bromo-4-(4-chloro-benzenesulfonyl)-6-methyl-3,4-dihydro-2H-benzo[1,4]oxazine 4-Chloro-benzenesulfonyl chloride (560 mg, 2.65 mmol) was added in small portions under nitrogen to an ice-cold solution of 8-bromo-6-methyl-3,4-dihydro-2H-benzo[1,4]oxazine (550 mg, 2.41 mmol) and pyridine (381 mg, 4.82 mmol) in dichloromethane (20 mL). After 12 hours at ambient temperature, water was added. The layers were separated. The organic phase was washed with saturated aqueous solution of sodium bicarbonate (20 mL), dried ($Na_2SO_4$) and concentrated to give the title compound as a solid (820 mg, 84%). A sample was recrystallized from ethanol. MS: $M^+$=401. M.p. 143.0-145.1° C.

Similarly, the following compounds were prepared:

8-Bromo-4-(3,4-dichloro-benzenesulfonyl)-6-methyl-3,4-dihydro-2H-benzo[1,4]oxazine as a white powder. MS: $M^+$=435. M.p. 150-151° C.

4-Benzenesulfonyl-8-bromo-6-chloro-3,4-dihydro-2H-benzo[1,4]oxazine. MS: $M^+$=387.

8-Bromo-6-chloro-4-(2-chloro-benzenesulfonyl)-3,4-dihydro-2H-benzo[1,4]oxazine as a white solid. MS: $M^+$=422.

8-Bromo-6-chloro-4-(2-fluoro-benzenesulfonyl)-3,4-dihydro-2H-benzo[1,4]oxazine as a white solid. MS: $M^+$=405.

8-Bromo-6-chloro-4-(naphthalene-1-sulfonyl)-3,4-dihydro-2H-benzo[1,4]oxazine as a white solid. MS: $M^+$=437.

8-Bromo-4-(3-chloro-benzenesulfonyl)-3,4-dihydro-2H-benzo[1,4]oxazine as an oil which solidified upon standing.

Using the above procedure, but starting with 8-bromo-2,2-dimethyl-3,4-dihydro-2H-benzo[1,4]oxazine (prepared by reducing 8-bromo-2,2-dimethyl-4H-benzo[1,4]oxazin-3-one, which in turn was prepared from 2-amino-6-bromophenol and 2-bromo-2-methylproprionyl bromide via the procedure described by Van Hes et al., WO 01/14330) and 2-fluorobenzenesulfonyl chloride, 8-bromo-4-(2-fluorobenzenesulfonyl)-2,2-dimethyl-3,4-dihydro-2H-benzo[1,4]oxazine was obtained as a white solid. MP.: 108.0-110.1°.

In another variation of the above procedure, 8-bromo-6-methyl-3,4-dihydro-2H-benzo[1,4]oxazine was replaced with 4-bromo-6,7,8,9-tetrahydro-5-oxa-9-aza-benzocycloheptene (obtained by reduction of 4-bromo-6,7-dihydro-9H-5-oxa-9-aza-benzocyclohepten-8-one, which in turn was prepared by reaction of 2-amino-6-bromophenol with 3-chloropropionyl chloride as described by Combs et al.; J. Med. Chem.; 33; 380-386 1990). Reaction of 4-bromo-6,7,8,9-tetrahydro-5-oxa-9-aza-benzocycloheptene with benzenesulfonyl chloride yielded 9-benzenesulfonyl-4-bromo-6,7,8,9-tetrahydro-5-oxa-9-aza-benzocycloheptene as a white solid, MS: $M^+$=336.

Step 2

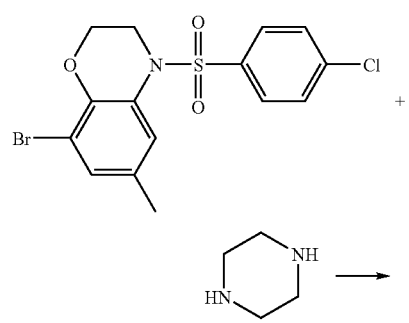

+

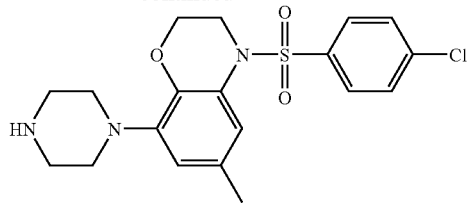

-continued

Method A: Synthesis of 4-(4-chloro-benzenesulfonyl)-6-methyl-8-piperazin-1-yl-3,4-dihydro-2H-benzo[1,4]oxazine A three neck flask was charged with tris(dibenzylideneacetone)dipalladium(0) (9.1 mg, 0.001 mmol, 2 mol % Pd), (±)-2,2'-bis(diphenylphosphino)-1,1'-binaphthyl (15.5 mg, 0.025 mmol, 5 mol %), and sodium-tert-butoxide (67 mg, 0.7 mmol) and flushed with nitrogen. A solution of 8-bromo-4-(4-chloro-benzenesulfonyl)-6-methyl-3,4-dihydro-2H-benzo[1,4]oxazine (201 mg, 0.5 mmol) and piperazine (129 mg, 1.5 mmol) in toluene (5 mL) was added. The mixture was heated to 95° C. and stirred for 18 hours. The mixture was cooled to room temperature, taken up in ethyl acetate and filtered. The organic phase was washed with water (2×20 mL) and extracted into 10% aqueous HCl (2×20 mL). The combined aqueous extracts were basified with solid potassium carbonate and extracted into ethyl acetate (2×20 mL). The combined organic extract was dried ($K_2CO_3$), filtered and concentrated to give the title compound as an oil (163 mg, 79.6%). The hydrochloride salt was prepared from ethanol-hydrogen chloride. MS: $MH^+$=408. M.p. 147.9-152.9° C.

Similarly, using the appropriate aryl- and heteroaryl-sulfonyl chlorides, the following compounds were prepared:

4-(3,4-Dichloro-benzenesulfonyl)-6-methyl-8-piperazin-1-yl-3,4-dihydro-2H-benzo[1,4]oxazine as white powder. MS: $MH^+$=442. M.p. 257-261° C.

4-(4-Chloro-benzenesulfonyl)-8-(3,5-dimethyl-piperazin-1-yl)-6-methyl-3,4-dihydro-2H-benzo[1,4]oxazine as a off-white solid. MS: $MH^+$=436. M.p. 171.8-185.8° C.

Similarly, using 8-bromo-4-(2-fluorobenzenesulfonyl)-2,2-dimethyl-3,4-dihydro-2H-benzo[1,4]oxazine, 4-(2-Fluoro-benzenesulfonyl)-2,2-dimethyl-8-piperazin-1-yl-3,4-dihydro-2H-benzo[1,4]oxazine was prepared as hydrochloride salt. MS: $MH^+$=406.

Similarly, using 9-benzenesulfonyl-4-bromo-6,7,8,9-tetrahydro-5-oxa-9-aza-benzocycloheptene, 9-Benzenesulfonyl-4-piperazin-1-yl-6,7,8,9-tetrahydro-5-oxa-9-aza-benzocycloheptene was prepared as a hydrochloride salt. MP.: 225.7-226.8.

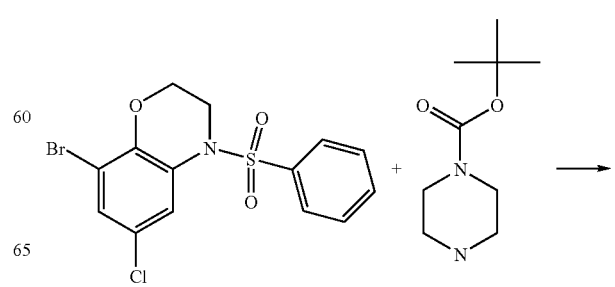

-continued

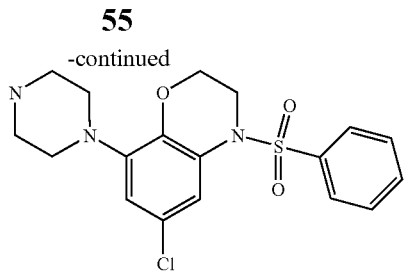

Method B: Synthesis of 4-benzenesulfonyl-6-chloro-8-piperazin-1-yl-3,4-dihydro-2H-benzo[1,4]oxazine A three neck flask was charged with tris(dibenzylideneacetone)dipalladium(0) (6.4 mg, 0.007 mmol, 2 mol % Pd), racemic-2,2'-bis(diphenylphosphino)-1,1'-binaphthyl (10.8 mg, 0.017 mmol, 5 mol %), and sodium tert-butoxide (47 mg, 0.48 mmol) and flushed with nitrogen. A solution of 4-benzenesulfonyl-8-bromo-6-chloro-3,4-dihydro-2H-benzo[1,4]oxazine (165 mg, 0.35 mmol) and piperazine-1-carboxylic acid tert-butyl ester (71.1 mg, 0.38 mmol) in toluene (2 mL) was added. The mixture was heated to 95° C. and stirred for 12 hours. The mixture was cooled to room temperature, taken up in ethyl acetate, filtered and concentrated. The crude material was purified by flash chromatography on silica gel (eluting with hexane-ethyl acetate; 7:3, v/v) to give 4-(4-Benzenesulfonyl-6-chloro-3,4-dihydro-2H-benzo[1,4]oxazin-8-yl)-piperazine-1-carboxylic acid tert-butyl ester as an oil (129 mg, 75%). MS: MH$^+$=494. The crude material was dissolved in ethanol (1 mL) and was treated with a solution of 10% hydrogen chloride in ethanol (1 mL). The mixture was heated on a steam bath for 15 minutes. White crystals precipitated upon cooling to room temperature. The solid was collected, washed with cold ethanol. Drying under vacuum gave 4-benzenesulfonyl-6-chloro-8-piperazin-1-yl-3,4-dihydro-2H-benzo[1,4]oxazine, hydrochloride salt as a white powder (90 mg, 73%). MS: MH$^+$=394. M.p. 202-205° C.

Similarly, the following compounds were prepared.

6-Chloro-4-(2-chloro-benzenesulfonyl)-8-piperazin-1-yl-3,4-dihydro-2H-benzo[1,4]oxazine, hydrochloride salt as a white powder. MS: MH$^+$=428. M.p.>250° C.

6-Chloro-4-(3-chloro-benzenesulfonyl)-8-piperazin-1-yl-3,4-dihydro-2H-benzo[1,4]oxazine, hydrochloride salt as a white powder. MS: MH$^+$=428. M.p. 193.4-196.5° C.

6-Chloro-4-(2-fluoro-benzenesulfonyl)-8-piperazin-1-yl-3,4-dihydro-2H-benzo[1,4]oxazine, hydrochloride salt as a white powder. MS: MH$^+$=412. M.p. 194.8-204.5° C.

6-Chloro-4-(naphthalene-1-sulfonyl)-8-piperazin-1-yl-3,4-dihydro-2H-benzo[1,4]oxazine, hydrochloride salt as a white powder. MS: MH$^+$=444. M.p. 273.7-276.6° C.

Similarly, but replacing piperazine-1-carboxylic acid tert-butyl ester with [1,4]diazepane-1-carboxylic acid tert-butyl ester and 4-benzenesulfonyl-8-bromo-6-chloro-3,4-dihydro-2H-benzo[1,4]oxazine with 8-bromo-4-(3-chloro-benzenesulfonyl)-3,4-dihydro-2H-benzo[1,4]oxazine the following compound was prepared:

4-(3-Chloro-benzenesulfonyl)-8-[1,4]diazepan-1-yl-3,4-dihydro-2H-benzo[1,4]oxazine, hydro chloride salt as a white powder. MS: MH$^+$=408. M.p. 175.9-180.3° C.

Example 4

This example illustrates a method for preparing 8-bromo-2,3-dihydro-benzo[1,4]oxazine.

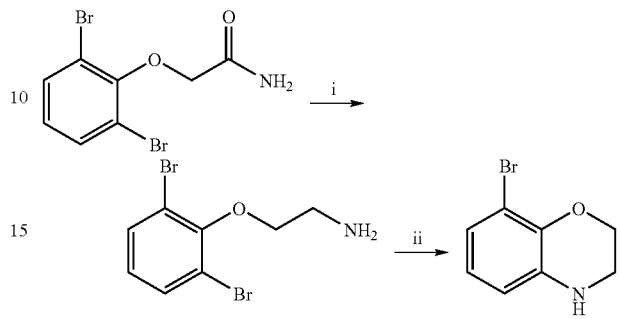

A solution of 2-(2,6-dibromo-phenoxy)acetamide (9.3 g, 0.03 mol) in tetrahydrofuran (100 mL) was heated to reflux and borane-dimethylsulfide (4.5 mL, 0.045 mL) was added in drops over a period of 15 min. After 3 h, 20 mL of ethanolic hydrogen chloride (2M, 0.4 mol) was added. The solution was refluxed for 30 min. Upon cooling to ambient temperature a white solid precipitated which was filtered and washed with diethyl ether (20 mL) to give 2-(2,6-dibromo-phenoxy)ethylamine, hydrochloride salt (7.25 g, 73.3%). MS: MH$^+$=294. M.p. 249.7-252.3° C.

A three neck flask was charge with tris(dibenzylideneacetone)dipalladium(0) (0.37 g, 0.0004 mol, 2 mol % Pd), (±) racemic-2,2'-bis(diphenylphosphino)-1,1'-binaphthyl (0.64 g, 0.001 mol, 5 mol % Pd), and sodium tert-butoxide (2.7 g, 0.028 mol) and flushed with nitrogen. A solution of 2-(2,6-dibromo-phenoxy)ethylamine (6 g, 0.02 mol) in toluene (50 mL) was added. The mixture was heated to 95° C. and was stirred for 12 h. The mixture was cooled to room temperature, taken up in ethyl acetate, filtered and concentrated. The crude material was purified by flash chromatography on silica gel (eluting with hexane-ethyl acetate; 7:3, v/v) to give 8-bromo-3,4-dihydro-2H-benzo[1,4]oxazine as an oil (275 mg, 48%). The hydrochloride salt was prepared from ethanol-hydrogen chloride. MS: MH$^+$=214. M.p. 184.1-195.4° C.

The synthesis of 6-bromo-3,4-dihydro-2H-benz[1,4]oxazine is reported in the following reference. Nugiel, David A.; Jacobs, Kim; Cornelius, Lyndon; Chang, Chong-Hwan; Jadhav, Prabhakar K.; et al; J. Med. Chem.; 40; 10; 1997: 1465-1474. 6-bromo-3,4-dihydro-2H-benz[1,4]oxazine may be used in the procedures of Example 1 and 2 to provide the corresponding compounds of Formula I.

Example 5

This example illustrates in vitro radioligand binding studies of Compound of Formula I.

The binding activity of compounds of this invention in vitro was determined as follows. Duplicate determinations of ligand affinity are made by competing for binding of [$^3$H] LSD in cell membranes derived from HEK293 cells stably expressing recombinant human 5-HT6 receptor. This cell line was prepared by the method described by Monsma et al., *Molecular Pharmacology*, Vol. 43 pp. 320-327 (1993).

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [$^3$H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [³H] LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left(\frac{B\text{max} - \text{basal}}{1 + 10^{-Hill(\log[\text{ligand}] - \log IC_{50})}}\right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of Example 5, compounds of Formula I were tested and found to be selective 5-HT6 antagonists.

Example 6

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of the formula:

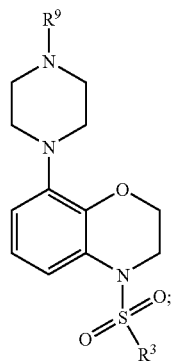

or a pharmaceutically acceptable salt thereof, wherein:
$R^3$ is alkyl, aryl, haloalkyl, heterocyclyl, or heteroaryl; and
$R^9$ is hydrogen, alkyl, cycloalkyl, cycloalkylalkyl or benzyl.

2. The compound of claim 1, wherein $R^3$ is aryl or heteroaryl.

3. The compound of claim 2, wherein $R^9$ is hydrogen or alkyl.

4. The compound of claim 3, wherein $R^3$ is optionally substituted phenyl.

5. The compound of claim 4, wherein $R^9$ is hydrogen or methyl.

6. The compound of claim 5, wherein $R^3$ is phenyl, 2-fluorophenyl, 2-chlorophenyl, 3,4-dichlorophenyl, 4-chlorophenyl, 3-chlorophenyl, 4-methoxyphenyl, 3,5-dichlorophenyl, 2,3-dichlorophenyl, 2,6-dichlorophenyl, 2,4-dichlorophenyl, 3-methanesulfonylaminophenyl, 2-methanesulfonylphenyl, 2-carbamoylphenyl, 3-methanesulfonylphenyl, 4-methanesulfonylphenyl, 3-fluorophenyl, naphthylene-1-yl, 2,4-difluorophenyl, 2-cyanophenyl, 2-chloro-4-fluorophenyl, 5-fluoro-2-methylphenyl, 5-chloronaphthyl, naphthylene-2-yl, 4-fluoro-2-methylphenyl, 2-hydroxyphenyl, 2-methoxyphenyl, 4-(piperazin-1-yl)-phenyl, or 2,3-dihydrobenzo[1,4]dioxinyl.

7. The compound of claim 5, wherein $R^3$ is optionally substituted heteroaryl.

8. The compound of claim 7, wherein $R^3$ is quinolin-8-yl, thiophen-2-yl, 5-chlorothiophen-2-yl, isoquinolin-5-yl, 4-(Benzo[1,2,5]thiadiazole-4-yl, 1-methyl-1H-imidazole-4-yl, or 4-(Benzo[1,2,5]oxadiazole-4-yl.

9. The compound of claim 4, wherein $R^3$ is 2-halophenyl.

10. The compound of claim 1, wherein $R^3$ is 2-fluorophenyl.

11. The compound of claim 1, wherein $R^9$ is hydrogen.

12. A compound of claim 1, wherein said compound is selected from the group consisting of:
4-Benzenesulfonyl-6-methyl-8-piperazin-1-yl-3,4-dihydro-2H-benzo[1,4]oxazine;
4-(2-Chloro-benzenesulfonyl)-6-methyl-8-piperazin-1-yl-3,4-dihydro-2H-benzo[1,4]oxazine;
4-(3,4-Dichloro-benzenesulfonyl)-6-methyl-8-piperazin-1-yl-3,4-dihydro-2H-benzo[1,4]oxazine;
4-(4-Chloro-benzenesulfonyl)-6-methyl-8-piperazin-1-yl-3,4-dihydro-2H-benzo[1,4]oxazine;
4-(4-Chloro-benzenesulfonyl)-8-(3,5-dimethyl-piperazin-1-yl)-6-methyl-3,4-dihydro-2H-benzo[1,4]oxazine;
6-Chloro-4-(2-chloro-benzenesulfonyl)-8-piperazin-1-yl-3,4-dihydro-2H-benzo[1,4]oxazine;
4-(2-Chloro-benzenesulfonyl)-8-piperazin-1-yl-3,4-dihydro-2H-benzo[1,4]oxazine;
4-(4-Chloro-benzenesulfonyl)-8-piperazin-1-yl-3,4-dihydro-2H-benzo[1,4]oxazine;
4-(4-Methoxy-benzenesulfonyl)-8-piperazin-1-yl-3,4-dihydro-2H-benzo[1,4]oxazine;
8-piperazin-1-yl-4-(quinoline-8-sulfonyl)-3,4-dihydro-2H-benzo[1,4]oxazine;
4-(3,4-Dichloro-benzenesulfonyl)-8-piperazin-1-yl-3,4-dihydro-2H-benzo[1,4]oxazine;
4-(3-Chloro-benzenesulfonyl)-8-piperazin-1-yl-3,4-dihydro-2H-benzo[1,4]oxazine;
4-(3,5-Dichloro-benzenesulfonyl)-8-piperazin-1-yl-3,4-dihydro-2H-benzo[1,4]oxazine;
4-(2,3-Dichloro-benzenesulfonyl)-8-piperazin-1-yl-3,4-dihydro-2H-benzo[1,4]oxazine;
4-(2,6-Dichloro-benzenesulfonyl)-8-piperazin-1-yl-3,4-dihydro-2H-benzo[1,4]oxazine;

4-(2,4-Dichloro-benzenesulfonyl)-8-piperazin-1-yl-3,4-dihydro-2H-benzo[1,4]oxazine;
N-[3-(8-piperazin-1-yl-2,3-dihydro-benzo[1,4]oxazine-4-sulfonyl)-phenyl]-methanesulfonamide;
N-[2-(8-piperazin-1-yl-2,3-dihydro-benzo[1,4]oxazine-4-sulfonyl)-phenyl]-methanesulfonamide;
2-(8-piperazin-1-yl-2,3-dihydro-benzo[1,4]oxazine-4-sulfonyl)-benzamide;
4-(3-Methanesulfonyl-benzenesulfonyl)-8-piperazin-1-yl-3,4-dihydro-2H-benzo[1,4]oxazine;
6-Chloro-4-(4-methanesulfonyl-benzenesulfonyl)-8-piperazin-1-yl-3,4-dihydro-2H-benzo[1,4]oxazine;
4-Benzenesulfonyl-8-piperazin-1-yl-3,4-dihydro-2H-benzo[1,4]oxazine;
4-(2-Fluoro-benzenesulfonyl)-8-piperazin-1-yl-3,4-dihydro-2H-benzo[1,4]oxazine;
4-(3-Fluoro-benzenesulfonyl)-8-piperazin-1-yl-3,4-dihydro-2H-benzo[1,4]oxazine;
4-Benzenesulfonyl-6-chloro-8-piperazin-1-yl-3,4-dihydro-2H-benzo[1,4]oxazine;
6-Chloro-4-(2-fluoro-benzenesulfonyl)-8-piperazin-1-yl-3,4-dihydro-2H-benzo[1,4]oxazine;
6-Chloro-4-(naphthalene-1-sulfonyl)-8-piperazin-1-yl-3,4-dihydro-2H-benzo[1,4]oxazine;
4-(2-methanesulfonyl-benzenesulfonyl)-8-piperazin-1-yl-3,4-dihydro-2H-benzo[1,4]oxazine;
6-Chloro-8-piperazin-1-yl-4-(thiophene-2-sulfonyl)-3,4-dihydro-2H-benzo[1,4]oxazine;
6-Chloro-8-piperazin-1-yl-4-(quinoline-8-sulfonyl)-3,4-dihydro-2H-benzo[1,4]oxazine;
6-Chloro-4-(3-fluoro-benzenesulfonyl)-8-piperazin-1-yl-3,4-dihydro-2H-benzo[1,4]oxazine;
6-Chloro-4-(2,4-difluoro-benzenesulfonyl)-8-piperazin-1-yl-3,4-dihydro-2H-benzo[1,4]oxazine;
6-Chloro-4-(5-chloro-thiophene-2-sulfonyl)-8-piperazin-1-yl-3,4-dihydro-2H-benzo[1,4]oxazine;
6-Chloro-4-(3-chloro-benzenesulfonyl)-8-piperazin-1-yl-3,4-dihydro-2H-benzo[1,4]oxazine;
6-Chloro-4-(2,3-dichloro-benzenesulfonyl)-8-piperazin-1-yl-3,4-dihydro-2H-benzo[1,4]oxazine;
2-(6-Chloro-8-piperazin-1-yl-2,3-dihydro-benzo[1,4]oxazine-4-sulfonyl)-benzonitrile;
6-Chloro-4-(2-chloro-4-fluoro-benzenesulfonyl)-8-piperazin-1-yl-3,4-dihydro-2H-benzo[1,4]oxazine;
6-Chloro-4-(5-fluoro-2-methyl-benzenesulfonyl)-8-piperazin-1-yl-3,4-dihydro-2H-benzo[1,4]oxazine;
6-Chloro-4-(5-chloro-naphthalene-1-sulfonyl)-8-piperazin-1-yl-3,4-dihydro-2H-benzo[1,4]oxazine;
6-Chloro-4-(isoquinoline-5-sulfonyl)-8-piperazin-1-yl-3,4-dihydro-2H-benzo[1,4]oxazine;
4-(Benzo[1,2,5]thiadiazole-4-sulfonyl)-6-chloro-8-piperazin-1-yl-3,4-dihydro-2H-benzo[1,4]oxazine;
6-Chloro-4-(1-methyl-1H-imidazole-4-sulfonyl)-8-piperazin-1-yl-3,4-dihydro-2H-benzo[1,4]oxazine;
4-(Benzo[1,2,5]oxadiazole-4-sulfonyl)-6-chloro-8-piperazin-1-yl-3,4-dihydro-2H-benzo[1,4]oxazine;
4-(2-Fluoro-benzenesulfonyl)-6-methyl-8-piperazin-1-yl-3,4-dihydro-2H-benzo[1,4]oxazine;
2-(6-Methyl-8-piperazin-1-yl-2,3-dihydro-benzo[1,4]oxazine-4-sulfonyl)-benzonitrile;
6-Methyl-8-piperazin-1-yl-4-(thiophene-2-sulfonyl)-3,4-dihydro-2H-benzo[1,4]oxazine;
6-Methyl-8-piperazin-1-yl-4-(quinoline-8-sulfonyl)-3,4-dihydro-2H-benzo[1,4]oxazine;
4-(3-Fluoro-benzenesulfonyl)-6-methyl-8-piperazin-1-yl-3,4-dihydro-2H-benzo[1,4]oxazine;
4-(2,4-Difluoro-benzenesulfonyl)-6-methyl-8-piperazin-1-yl-3,4-dihydro-2H-benzo[1,4]oxazine;
4-(2-Chloro-4-fluoro-benzenesulfonyl)-6-methyl-8-piperazin-1-yl-3,4-dihydro-2H-benzo[1,4]oxazine;
4-(5-Fluoro-2-methyl-benzenesulfonyl)-6-methyl-8-piperazin-1-yl-3,4-dihydro-2H-benzo[1,4]oxazine;
4-(Isoquinoline-5-sulfonyl)-6-methyl-8-piperazin-1-yl-3,4-dihydro-2H-benzo[1,4]oxazine;
6-Methyl-4-(1-methyl-1H-imidazole-4-sulfonyl)-8-piperazin-1-yl-3,4-dihydro-2H-benzo[1,4]oxazine;
4-(2-Fluoro-benzenesulfonyl)-6-methoxy-8-piperazin-1-yl-3,4-dihydro-2H-benzo[1,4]oxazine;
6-Chloro-4-(2-fluoro-benzenesulfonyl)-8-(4-methyl-piperazin-1-yl)-3,4-dihydro-2H-benzo[1,4]oxazine;
6-Fluoro-4-(2-fluoro-benzenesulfonyl)-8-piperazin-1-yl-3,4-dihydro-2H-benzo[1,4]oxazine;
4-(3-Methanesulfonyl-benzenesulfonyl)-8-(4-methyl-piperazin-1-yl)-3,4-dihydro-2H-benzo[1,4]oxazine;
6-Chloro-8-(4-methyl-piperazin-1-yl)-4-(naphthalene-2-sulfonyl)-3,4-dihydro-2H-benzo[1,4]oxazine;
4-Benzenesulfonyl-8-(4-methyl-piperazin-1-yl)-3,4-dihydro-2H-benzo[1,4]oxazine;
4-(2-Fluoro-benzenesulfonyl)-8-(4-methyl-piperazin-1-yl)-3,4-dihydro-2H-benzo[1,4]oxazine;
4-Benzenesulfonyl-6-methoxy-8-piperazin-1-yl-3,4-dihydro-2H-benzo[1,4]oxazine;
4-Benzenesulfonyl-6-fluoro-8-piperazin-1-yl-3,4-dihydro-2H-benzo[1,4]oxazine;
2-(8-piperazin-1-yl-2,3-dihydro-benzo[1,4]oxazine-4-sulfonyl)-phenol;
4-(2-Methoxy-benzenesulfonyl)-8-piperazin-1-yl-3,4-dihydro-2H-benzo[1,4]oxazine;
4-(2,3-Dihydro-benzo[1,4]dioxine-6-sulfonyl)-6-methoxy-8-piperazin-1-yl-3,4-dihydro-2H-benzo[1,4]oxazine;
4-(2,3-Dihydro-benzo[1,4]dioxine-6-sulfonyl)-6-fluoro-8-piperazin-1-yl-3,4-dihydro-2H-benzo[1,4]oxazine;
6-Methoxy-4-(naphthalene-1-sulfonyl)-8-piperazin-1-yl-3,4-dihydro-2H-benzo[1,4]oxazine;
4-(2-Chloro-benzenesulfonyl)-6-methoxy-8-piperazin-1-yl-3,4-dihydro-2H-benzo[1,4]oxazine;
4-(3-Chloro-benzenesulfonyl)-6-methoxy-8-piperazin-1-yl-3,4-dihydro-2H-benzo[1,4]oxazine;
4-(5-Fluoro-2-methyl-benzenesulfonyl)-6-methoxy-8-piperazin-1-yl-3,4-dihydro-2H-benzo[1,4]oxazine;
6-Methoxy-8-piperazin-1-yl-4-(toluene-2-sulfonyl)-3,4-dihydro-2H-benzo[1,4]oxazine;
2-(6-Methyl-8-piperazin-1-yl-2,3-dihydro-benzo[1,4]oxazine-4-sulfonyl)-phenol;
6-tert-Butyl-4-(2-fluoro-benzenesulfonyl)-8-piperazin-1-yl-3,4-dihydro-2H-benzo[1,4]oxazine; and
6-piperazin-1-yl-4-(4-piperazin-1-yl-benzenesulfonyl)-3,4-dihydro-2H-benzo[1,4]oxazine.

13. A composition comprising:
(a) a therapeutically effective amount of a compound of claim 1; and
(b) a pharmaceutically acceptable carrier.

14. The compound of claim 12, wherein said compound is selected from:
4-(2-Fluoro-benzenesulfonyl)-8-piperazin-1-yl-3,4-dihydro-2H-benzo[1,4]oxazine;
6-Chloro-4-(2-fluoro-benzenesulfonyl)-8-piperazin-1-yl-3,4-dihydro-2H-benzo[1,4]oxazine;
4-(2-Fluoro-benzenesulfonyl)-6-methyl-8-piperazin-1-yl-3,4-dihydro-2H-benzo[1,4]oxazine;
4-(2-Fluoro-benzenesulfonyl)-6-methoxy-8-piperazin-1-yl-3,4-dihydro-2H-benzo[1,4]oxazine;

6-Chloro-4-(2-fluoro-benzenesulfonyl)-8-(4-methyl-piperazin-1-yl)-3,4-dihydro-2H-benzo[1,4]oxazine;
6-Fluoro-4-(2-fluoro-benzenesulfonyl)-8-piperazin-1-yl-3,4-dihydro-2H-benzo[1,4]oxazine;
4-(2-Fluoro-benzenesulfonyl)-8-(4-methyl-piperazin-1-yl)-3,4-dihydro-2H-benzo[1,4]oxazine; and
6-tent-Butyl-4-(2-fluoro-benzenesulfonyl)-8-piperazin-1-yl-3,4-dihydro-2H-benzo[1,4]oxazine.

15. The compound 4-(2-Fluoro-benzenesulfonyl)-8-piperazin-1-yl-3,4-dihydro-2H-benzo[1,4]oxazine, or a pharmaceutically acceptable salt thereof.

16. The compound 4-(2-Fluoro-benzenesulfonyl)-6-methyl-8-piperazin-1-yl-3,4-dihydro-2H-benzo[1,4]oxazine, or a pharmaceutically acceptable salt thereof.

* * * * *